(12) United States Patent
Inomata et al.

(10) Patent No.: US 7,824,855 B2
(45) Date of Patent: Nov. 2, 2010

(54) METHOD FOR SELECTIVELY SEPARATING AND PURIFYING RNA AND METHOD FOR SEPARATING AND PURIFYING NUCLEIC ACID

(75) Inventors: Hiroko Inomata, Asaka (JP); Rie Iwata, Asaka (JP)

(73) Assignee: FUJIFILM Corporation, Tokyo (JP)

( * ) Notice: Subject to any disclaimer, the term of this patent is extended or adjusted under 35 U.S.C. 154(b) by 592 days.

(21) Appl. No.: 10/593,183

(22) PCT Filed: Mar. 25, 2005

(86) PCT No.: PCT/JP2005/006423

§ 371 (c)(1), (2), (4) Date: Sep. 18, 2006

(87) PCT Pub. No.: WO2005/093052

PCT Pub. Date: Oct. 6, 2005

(65) Prior Publication Data

US 2008/0248559 A1    Oct. 9, 2008

(30) Foreign Application Priority Data

| Mar. 26, 2004 | (JP) | 2004-091681 |
| Mar. 26, 2004 | (JP) | 2004-092000 |
| Aug. 2, 2004 | (JP) | 2004-225286 |
| Feb. 3, 2005 | (JP) | 2005-027918 |
| Feb. 4, 2005 | (JP) | 2005-029177 |
| Mar. 3, 2005 | (JP) | 2005-059057 |
| Mar. 18, 2005 | (JP) | 2005-080040 |
| Mar. 22, 2005 | (JP) | 2005-082283 |

(51) Int. Cl.
- *C12Q 1/68* (2006.01)
- *C07H 21/00* (2006.01)
- *C07H 21/02* (2006.01)
- *C07H 21/04* (2006.01)

(52) U.S. Cl. .......... 435/6; 536/23.1; 536/24.3; 536/25.4

(58) Field of Classification Search .......... 435/6; 536/22.1, 23.1, 24.3, 25.4
See application file for complete search history.

(56) References Cited

U.S. PATENT DOCUMENTS

| 4,935,342 A | * | 6/1990 | Seligson et al. | 435/6 |
| 4,980,456 A | * | 12/1990 | Scandella et al. | 530/383 |
| 5,075,430 A | * | 12/1991 | Little | 536/25.41 |
| 5,155,018 A | * | 10/1992 | Gillespie et al. | 536/23.1 |
| 5,234,809 A | * | 8/1993 | Boom et al. | 435/91.2 |
| 5,405,951 A | | 4/1995 | Woodard | |
| 5,606,046 A | * | 2/1997 | Woodard et al. | 536/25.4 |
| 5,645,723 A | | 7/1997 | Fujishiro et al. | |
| 5,650,506 A | * | 7/1997 | Woodard et al. | 536/25.4 |
| 5,824,224 A | | 10/1998 | Fujishiro et al. | |
| 6,204,375 B1 | * | 3/2001 | Lader | 536/25.4 |
| 6,218,531 B1 | * | 4/2001 | Ekenberg | 536/25.41 |
| 6,905,825 B2 | | 6/2005 | Kojima et al. | |
| 2002/0192667 A1 | | 12/2002 | Kojima et al. | |
| 2003/0152974 A1 | | 8/2003 | Gauch et al. | |
| 2003/0170664 A1 | | 9/2003 | Mori et al. | |
| 2004/0019196 A1 | * | 1/2004 | Bair et al. | 536/25.4 |
| 2004/0058370 A1 | | 3/2004 | Mori et al. | |
| 2004/0063122 A1 | | 4/2004 | Mori et al. | |
| 2004/0167324 A1 | | 8/2004 | Kojima et al. | |
| 2005/0026153 A1 | | 2/2005 | Iannotti et al. | |
| 2005/0026159 A1 | | 2/2005 | Robbins et al. | |
| 2005/0026175 A1 | | 2/2005 | Link et al. | |
| 2005/0042660 A1 | | 2/2005 | Hall et al. | |
| 2005/0095626 A1 | | 5/2005 | Komazawa et al. | |
| 2005/0112656 A1 | * | 5/2005 | Iwaki | 435/6 |
| 2005/0171333 A1 | | 8/2005 | Paulsen | |
| 2005/0244882 A1 | | 11/2005 | Gauch et al. | |

(Continued)

FOREIGN PATENT DOCUMENTS

EP    1380642 A1    1/2004

(Continued)

OTHER PUBLICATIONS

Thurman et al. Advances in solid-phase extractioon disks for environmental chemistry. Trends in Analytical Chemistry 19 (1) : 18-26 (2000).*

(Continued)

*Primary Examiner*—Ethan Whisenant
(74) *Attorney, Agent, or Firm*—Birch, Stewart, Kolasch & Birch, LLP.

(57) ABSTRACT

A method for selectively separating and purifying RNA from a mixture solution of nucleic acid containing DNA and RNA, wherein the method comprising the steps of: (1-a) adsorbing nucleic acid; (1-b) washing; (1-c) subjecting to a DNase treatment; (1-d) washing; and (1-e) desorbing the RNA from a nucleic acid-adsorbing porous membrane by a recovering solution, wherein in the step (1-c), a total amount of a DNase solution is 130 μl or less per 1 cm$^2$ of the membrane. And a method for selectively separating and purifying RNA or DNA, which comprises the steps of: (2-a) adsorbing nucleic acid; (2-b) washing by a washing solution; and (2-c) desorbing the nucleic acid from a nucleic acid-adsorbing porous membrane, wherein the washing solution contains a water-soluble organic solvent having a concentration of 50% by weight or less, and does not contain a chaotropic salt.

32 Claims, 5 Drawing Sheets

U.S. PATENT DOCUMENTS

| | | |
|---|---|---|
| 2006/0099605 A1 | 5/2006 | Hall et al. |
| 2006/0228731 A1* | 10/2006 | Latham et al. ............... 435/6 |
| 2006/0263775 A1* | 11/2006 | Kaplan ............................ 435/6 |
| 2007/0009893 A1 | 1/2007 | Mori et al. |
| 2007/0167514 A1* | 7/2007 | Moore et al. ............... 514/454 |
| 2007/0221563 A1 | 9/2007 | Sakaino et al. |
| 2008/0248559 A1 | 10/2008 | Inomata et al. |

FOREIGN PATENT DOCUMENTS

| | | |
|---|---|---|
| EP | 1382676 A1 | 1/2004 |
| EP | 1382677 A1 | 1/2004 |
| EP | 1512741 A2 | 3/2005 |
| JP | 5-268963 A | 10/1993 |
| JP | 7-51065 A | 6/1995 |
| JP | 9-47278 A | 2/1997 |
| JP | 9-327291 A | 12/1997 |
| JP | 2832586 B2 | 10/1998 |
| JP | 11-146783 A | 6/1999 |
| JP | 3058342 * | 4/2000 |
| JP | 2001-299344 A | 10/2001 |
| JP | 2001-520894 T | 11/2001 |
| JP | 2002-507121 T | 3/2002 |
| JP | 2002-360245 A | 12/2002 |
| JP | 2003-128691 A | 5/2003 |
| JP | 2003-204799 A | 7/2003 |
| JP | 2004-49106 A | 2/2004 |
| JP | 2004-49107 A | 2/2004 |
| JP | 2004-49108 A | 2/2004 |
| JP | 2004-242622 A | 9/2004 |
| JP | 2005-52142 A | 3/2005 |
| JP | 2005-95003 A | 4/2005 |
| JP | 2005-151975 A | 6/2005 |
| JP | 2005-192558 A | 7/2005 |
| JP | 2005-287498 A | 10/2005 |
| JP | 2006-238854 A | 9/2006 |
| JP | 2007-515959 T | 6/2007 |
| JP | 3983125 B2 | 7/2007 |
| WO | WO-98/59076 A1 | 12/1998 |
| WO | WO-2005/026347 A1 | 3/2005 |
| WO | WO-2005/037988 A2 | 4/2005 |
| WO | WO-2005/058933 A1 | 6/2005 |
| WO | WO-2006/083017 A1 | 8/2006 |
| WO | WO-2006/093330 A1 | 9/2006 |

OTHER PUBLICATIONS

Dolter et al., Bio-Techniques, vol. 30, No. 6, Jun. 2001, pp. 1358-1361. XP002476727.

Watson et al., Journal of Clinical Ligand Assay, vol. 21, No. 4, pp. 394-403, 1998. XP009078446.

Decision of Final Rejection of Japanese Patent Application No. 2005-082283 dispatched Jul. 6, 2010.

* cited by examiner

E2-2: EXAMPLE 2-2-2, ETHANOL CONCENTRATION 30.0%
E2-1: EXAMPLE 2-2-2, ETHANOL CONCENTRATION 20.0%
E1-1: EXAMPLE 2-2-1, ETHANOL CONCENTRATION 12.5%
E1-2: EXAMPLE 2-2-1, ETHANOL CONCENTRATION 10.0%
E1-3: EXAMPLE 2-2-1, ETHANOL CONCENTRATION 7.5%
E1-4: EXAMPLE 2-2-1, ETHANOL CONCENTRATION 5.0%
E2-3: EXAMPLE 2-2-2, ETHANOL CONCENTRATION 0.0%
M: 1kb PLUS LADDER

METHOD FOR SELECTIVELY SEPARATING AND PURIFYING RNA AND METHOD FOR SEPARATING AND PURIFYING NUCLEIC ACID

TECHNICAL FIELD

The present invention relates to a method for selectively separating and purifying RNA. Further, The present invention relates to a method for separating and purifying nucleic acid. Particularly, the invention relates to a method for separating and purifying RNA or DNA from a mixture of nucleic acid containing RNA and DNA. More particularly, the invention relates to a method for separating and purifying RNA or DNA from a mixture of nucleic acid containing RNA and DNA using a cartridge for separation and purification of nucleic acid comprising a container having at least two openings wherein the cartridge for separation and purification of nucleic acid receives the nucleic acid-adsorbing porous membrane in an inside of the container, and a pressure difference-generating apparatus.

BACKGROUND ART

Various forms of nucleic acid are used in a variety of fields. For example, in the field of a recombinant nucleic acid technology, the nucleic acid is required to be used in the form of a probe, a genomic nucleic acid and a plasmid nucleic acid.

Also, in the field of diagnostics, nucleic acid is used in various forms for various purposes. For example, nucleic acid probes are used routinely in the detection and diagnosis of human pathogen. Likewise, nucleic acid is used in the detection of genetic disorders. Nucleic acid is also used in the detection of food pollution substances. Further, nucleic acid is used routinely in locating, identifying and isolating nucleic acid of interest for a variety of reasons ranging from genetic mapping to cloning and recombinant expression.

In many cases, nucleic acid is available in extremely small amounts, and thus isolation and purification procedures are laborious and time consuming. Occasionally, these time consuming and laborious operations are likely to lead to the loss of nucleic acid.

In purifying nucleic acid from samples obtained from serum, urine and bacterial cultures, there is an additional risk of contamination and false-positive result.

One widely known separation and purification methods, there is a method in which nucleic acid is adsorbed to silicon dioxide, silica polymer, magnesium silicate or the like solid phase and then separated and purified by carrying out washing, desorption and the like operations (e.g., JPA-7-51065). This method is excellent in its separation performance, but cannot be said sufficient in terms of convenience, quickness and automation aptitude, and has problems in that the tools and apparatuses to be used in this method are not suited for automation and miniaturization, it is difficult to produce the tools and apparatuses, particularly an adsorption medium, in an industrially large scale with the same performance, and their handling is so inconvenient that they are difficult to be processed in various shapes. Further, due to the fragility of a material and requiring a certain thickness or more to obtain mechanical strength, especially, in order to homogeneously interact DNase on a solid phase when degrading DNA with DNase for selectively recovering RNA from a mixture sample containing DNA and RNA, there are drawbacks such as requiring the DNase solution in a certain amount or more. DNase is relatively expensive, so that this could become a problem in case of selectively recovering RNA which necessity is predicted to increase much more in the future.

Further, one of the methods for separating and purifying nucleic acid simply and effectively is to use a solution for adsorbing nucleic acid onto a solid phase and a solution for desorbing nucleic acid from the solid phase membrane so that there is provided a method for separating and purifying nucleic acid by adsorbing and desorbing onto and from the solid phase comprising an organic polymer having a hydroxyl group on a surface thereof (JPA-2003-128691 and JPA-2004-49108), but more improvement is demanded.

Examples of other related known methods for separating and purifying nucleic acid are using a centrifuge method, magnetic beads and a filter. Further, an apparatus for separating and purifying nucleic acid, which use these methods, have been proposed. For example, an apparatus for separating and purifying nucleic acid using filter, wherein several filter tubes receiving filters are set on a rack, and therein a sample solution containing nucleic acid is injected where the bottom portion of the rack is applied with a sealing agent and sealed with an air chamber to reduce an inner pressure. Simultaneously the sample solution containing nucleic acid is sucked from the discharging side and passed through all filter tube, so as to adsorb nucleic acid onto the filter. Afterwards, a washing solution and a recovering solution are injected and again sucked thereto under reduced pressure so that washing and desorbing are also conducted. An automated apparatus using these procedures has been proposed. (e.g., refer to Japanese Patent No. 2832586).

DISCLOSURE OF THE INVENTION

However, a method for separating and purifying DNA or RNA efficiently and with good precision from a mixture solution where DNA and RNA are in a mixed state has not been specifically disclosed in the related methods for separating and purifying nucleic acid.

Therefore, an first object of the present invention is to provide a more inexpensive method for selectively separating and purifying RNA from a mixture of nucleic acid containing RNA and DNA, which comprises adsorbing nucleic acid in a test sample onto a nucleic acid-adsorbing porous membrane and desorbing RNA via washing and the like. More specifically, it provides a more inexpensive and an excellent method in purity for selectively recovering RNA from a mixture sample of DNA and RNA, wherein the method employs the nucleic acid-adsorbing porous membrane having an excellent separating capability, a good washing efficiency, a simple and rapid workability and a good suitability for automation, and capable of being mass produced with a substantially identical separating capability.

Further, a second object of the present invention is to provide a more inexpensive separation and purification method which selectively recovers RNA or DNA from a mixture sample of RNA and DNA.

The present inventors have made intensive studies to solve the above first problem. As a result, they have found that aforementioned problem is achieved by employing a method for selectively separating and purifying RNA, which comprises adsorbing and desorbing a mixture of nucleic acid containing RNA and DNA onto and from a porous membrane by using a cartridge for separation and purification of nucleic acid comprising a container having two openings wherein the cartridge for separation and purification of nucleic acid receives the porous membrane in an inside of the container, wherein the method comprises a step of degrading DNA with DNase in the porous membrane, especially, wherein the step is conducted with a DNase solution amount of 130 μl or less per 1 cm² of the nucleic acid-adsorbing porous membrane, thus completed the present invention. That is, the invention comprises the following constitutions:

(1) A method for selectively separating and purifying RNA from a mixture solution of nucleic acid containing DNA and RNA, the method using a cartridge for separation and purification of nucleic acid comprising a container having at least two openings, and the cartridge receives a nucleic acid-adsorbing porous membrane which a solution can pass through in the container, wherein the method comprising the steps of:

(1-a) adsorbing nucleic acid to the nucleic acid-adsorbing porous membrane;

(1-b) washing the nucleic acid-adsorbing porous membrane by a washing solution, while the nucleic acid is adsorbed to the nucleic acid-adsorbing porous membrane;

(1-c) subjecting the nucleic acid-adsorbing porous membrane to a DNase treatment;

(1-d) washing the nucleic acid-adsorbing porous membrane by the washing solution; and (1-e) desorbing the RNA from the nucleic acid-adsorbing porous membrane by a recovering solution, so as to discharge the recovering solution from the cartridge, wherein in the step (1-c), a total amount of a DNase solution is 130 μl or less per 1 cm² of the nucleic acid-adsorbing porous membrane.

(2) The method for selectively separating and purifying RNA as described in (1) above, wherein the DNase solution has a DNase concentration of 10 to 10000 Kunitz U/mL.

(3) The method for selectively separating and purifying RNA as described in (1) or (2) above, wherein the nucleic acid adsorbing porous membrane comprises an organic polymer to which the nucleic acid is adsorbed by a weak interaction involving substantially no ionic bond.

(4) The method for selectively separating and purifying RNA as described in (3) above, wherein the nucleic acid-adsorbing porous membrane has a hydroxyl group.

(5) The method for selectively separating and purifying RNA as described in any of (1) to (4) above, wherein the nucleic acid adsorbing porous membrane comprises an organic material obtained by saponification of a mixture of acetyl celluloses different from each other in acetyl value.

(6) The method for selectively separating and purifying RNA as described in any of (1) to (5) above, wherein the nucleic acid adsorbing porous membrane has a front area and a back area asymmetrical with each other.

(7) The method for selectively separating and purifying RNA as described in any of (1) to (6) above, wherein the mixture solution of nucleic acid is a solution where a water-soluble organic solvent is further added to a mixed solution obtained by mixing a nucleic acid solubilizing reagent added to a test sample with the test sample.

(8) The method for selectively separating and purifying RNA as described in (7) above, wherein the test sample is a cultured cell.

(9) The method for selectively separating and purifying RNA as described in (8) above, wherein the cultured cell is a floating-type cell.

(10) The method for selectively separating and purifying RNA as described in (8) above, wherein the cultured cell is an adhesive-type cell.

(11) The method for selectively separating and purifying RNA as described in (7) above, wherein the test sample is an animal tissue.

(12) The method for selectively separating and purifying RNA as described in any of (7) to (11) above, wherein the test sample is homogenized before or after adding nucleic-acid solubilizing reagent.

(13) The method for selectively separating and purifying RNA as described in any of (7) to (12) above, wherein the nucleic acid-solubilizing reagent comprises at least one of a chaotropic salt, a nucleic acid stabilizing agent, a surfactant, a buffer and a defoaming agent.

(14) The method for selectively separating and purifying RNA as described in (13) above, wherein the chaotropic salt is at least one of a guanidine hydrochloride and a guanidine thiocyanate.

(15) The method for selectively separating and purifying RNA as described in any of (7) to (14) above, wherein the water-soluble organic solvent comprises at least one of methanol, ethanol, propanol and an isomer thereof, and butanol and an isomer thereof.

(16) The method for selectively separating and purifying RNA as described in any of (1) to (15) above, wherein the washing solution is a solution containing at least one alcohol selected from methanol, ethanol propanol and an isomer thereof, and butanol and an isomer thereof, wherein the washing solution contains said at least one alcohol in an amount of 1 to 100% by weight.

(17) The method for selectively separating and purifying RNA as described in any of (1) to (16) above, wherein the recovering solution is a solution having a salt concentration of 0.5 mol/L or less.

(18) The method for selectively separating and purifying RNA as described in any of (1) to (17) above, wherein a pressure difference-generating apparatus is a pump detachably connected to one opening of the cartridge for separation and purification of nucleic acid.

(19) A kit of a cartridge for separation and purification of nucleic acid and a reagent for performing a method as described in any (1) to (18) above.

(20) An apparatus for automatically performing a method as described in any of (1) to (18) above.

(21) An apparatus for automatically using a kit as described in (19) above.

Further, the present inventors have made intensive studies to solve the above second problem. As a result, they have found that, in a method for separating and purifying nucleic acid comprising adsorbing and desorbing a mixture of nucleic acid containing RNA and DNA onto and from a porous membrane, RNA or DNA can be selectively separated and purified by eluting DNA wherein a washing solution has an alcohol concentration of 50% by weight or less, and thus have completed the present invention. Further in the invention, by using a solution having a salt concentration of 0.5 M or less as a recovering solution, RNA can be separated and purified with a high purity and high yield. Additionally, in the invention, it is preferred to use a porous membrane as the porous membrane which the nucleic acid is adsorbed to by a weak interaction in which an ionic bond is not involved, for obtaining the effects of the invention. Further, it is preferred to use a cartridge for separation and purification of nucleic acid comprising a container having two openings wherein the cartridge for separation and purification of nucleic acid receives a porous membrane comprising an organic polymer in an inside of the container. That is, the invention comprises the following constitutions:

(22) A method for selectively separating and purifying RNA or DNA, which comprises the steps of:

(2-a) adsorbing nucleic acid to a nucleic acid-adsorbing porous membrane by passing a mixture solution of nucleic acid containing RNA and DNA through the nucleic acid-adsorbing porous membrane;

(2-b) washing the nucleic acid-adsorbing porous membrane by passing a washing solution through the nucleic acid-adsorbing porous membrane, while the nucleic acid is adsorbed to the nucleic acid-adsorbing porous membrane; and (2-c) desorbing the nucleic acid from the nucleic acid-adsorbing porous membrane by passing a recovering solution through the nucleic acid-adsorbing porous membrane, wherein the washing solution contains a water-soluble organic solvent having a concentration of 50% by weight or less, and the washing solution does not contain a chaotropic salt.

(23) The method for selectively separating and purifying RNA or DNA as described in (22) above, wherein the washing solution contains a water-soluble organic solvent having a concentration of 5 to 40% by weight.

(24) The method for selectively separating and purifying RNA or DNA as described in (22) or (23) above, wherein the nucleic acid-adsorbing porous membrane is a porous membrane comprising an organic polymer to which the nucleic acid is adsorbed by a weak interaction involving substantially no ionic bond.

(25) The method for selectively separating and purifying RNA or DNA as described in any of (22) to (24) above, wherein the nucleic acid-adsorbing porous membrane is a porous membrane comprising an organic polymer having a hydroxyl group.

(26) The method for selectively separating and purifying RNA or DNA as described in any of (22) to (25) above, wherein the nucleic acid-adsorbing porous membrane is a porous membrane comprising an organic material obtained by saponification of a mixture of acetyl celluloses different from each other in acetyl value.

(27) The method for selectively separating and purifying RNA or DNA as described in any of (22) to (26) above, wherein the nucleic acid-adsorbing porous membrane has a front area and a back area asymmetrical with each other.

(28) The method for selectively separating and purifying RNA or DNA as described in any of (22) to (27) above, wherein the sample solution is a solution where a water-soluble organic solvent is added to a solution obtained by treating a cell or virus-containing test sample with a nucleic acid-solubilizing reagent.

(29) The method for selectively separating and purifying RNA or DNA as described in (28) above, wherein the test sample is a cultured cell.

(30) The method for selectively separating and purifying RNA or DNA as described in (28) above, wherein the test sample is an animal tissue.

(31) The method for selectively separating and purifying RNA as described in any of (28) to (30) above, wherein the test sample is homogenized before or after adding nucleic-acid solubilizing reagent.

(32) The method for selectively separating and purifying RNA or DNA as described in (28) above, wherein the nucleic acid-solubilizing reagent comprises at least one of a chaotropic salt, a nucleic acid stabilizing agent, a surfactant, a buffer and a defoaming agent.

(33) The method for selectively separating and purifying RNA or DNA as described in (32) above, wherein the chaotropic salt is at least one of a guanidine hydrochloride and a guanidine thiocyanate.

(34) The method for selectively separating and purifying RNA or DNA as described in any of (22) to (33) above, wherein the water-soluble organic solvent is at least one alcohol selected from methanol, ethanol, propanol and an isomer thereof, and butanol and an isomer thereof.

(35) The method for selectively separating and purifying RNA or DNA as described in any of (22) to (34) above, wherein the washing solution is a solution containing at least one alcohol selected from methanol, ethanol, propanol and an isomer thereof, and butanol and an isomer thereof in an amount of 5 to 50% by weight.

(36) The method for selectively separating and purifying RNA as described in any of (22) to (35) above, wherein the washing solution contains water-soluble salt.

(37) The method for selectively separating and purifying RNA as described in (36) above, wherein the concentration of water-soluble salt is 10 mmol/L or more.

(38) The method for selectively separating and purifying RNA as described in (36) or (37) above, wherein the concentration of water-soluble salt is in a range of 10 mmol/L to 1 mol/L.

(39) The method for selectively separating and purifying RNA or DNA as described in any of (22) to (38) above, wherein the washing solution is a solution containing a chloride in an amount of 10 mmol/L to 1 mol/L.

(40) The method for selectively separating and purifying RNA or DNA as described in any of (22) to (39) above, wherein the recovering solution is a solution capable of desorbing an adsorbed RNA from the nucleic acid-adsorbing porous membrane having a salt concentration of 0.5 mol/L or less.

(41) The method for selectively separating and purifying RNA or DNA as described in any of (22) to (40) above, wherein in each of the steps of (2-a), (2-b) and (2-c), the sample solution containing the nucleic acid, the washing solution and the recovering solution are passed through the nucleic acid-adsorbing porous membrane by using (i) a cartridge for separation and purification of nucleic acid comprising a container having at least two openings, and the cartridge for separation and purification of nucleic acid receives the nucleic acid-adsorbing porous membrane which a solution can pass through in the container and (ii) a pressure difference-generating apparatus, wherein the pressure difference-generating apparatus is a pump detachably connected to one opening of the cartridge for separation and purification of nucleic acid.

(42) A kit of a cartridge for separation and purification of nucleic acid and a reagent for performing a method as described in any of (22) to (41) above.

(43) An apparatus for automatically performing a method as described in any of (22) to (41) above.

Figure 1:
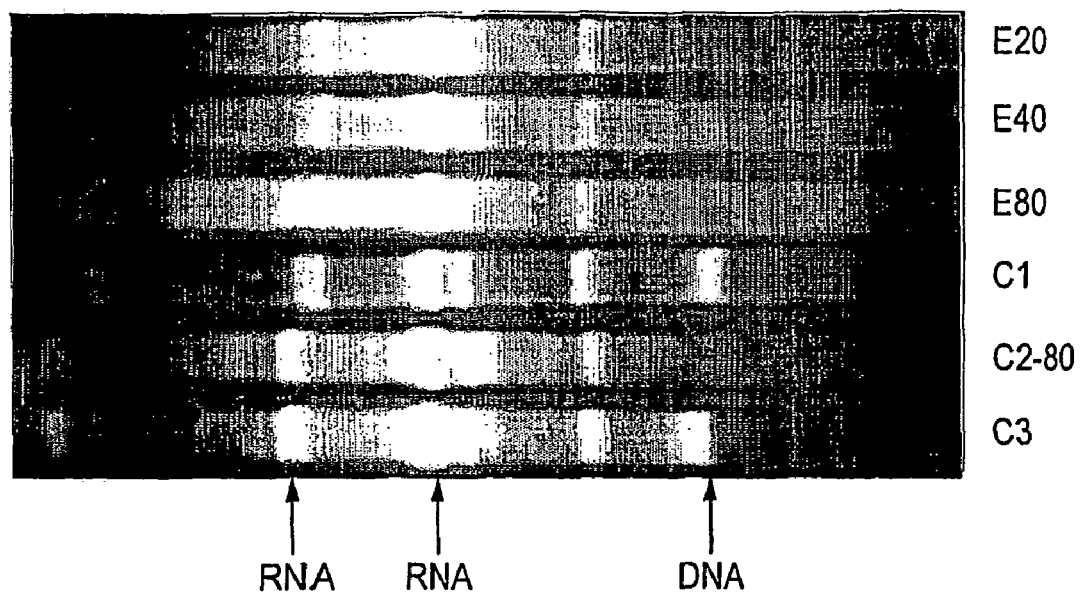
FIG. 1 is a view of a photo obtained by conducting electrophoresis using 1% agarose gel of the recovering solution containing recovered nucleic acid in accordance with Example 1-1 and Comparative Example 1-1, 1-2 and 1-3.

RNA denotes RNA derived band, DNA denotes DNA derived band, E10 denotes Example 1-1: DNase solution quantity 10 µl (26 µl/cm$^2$), E20 denotes Example 1-1: DNase solution quantity 20 µl (52 µl/cm$^2$), E40 denotes Example 1-1: DNase solution quantity 40 µl (104 µl/cm$^2$), E80 denotes Reference Example 1-1: DNase solution quantity 80 µl (208 µl/cm$^2$), C1 denotes Comparative Example 1-1: DNase solution quantity 0 µl, C2-10 denotes Comparative Example 1-2: DNase solution quantity 10 µl (26 µl/cm$^2$), C2-20 denotes Comparative Example 1-2: DNase solution quantity 20 µl (52 µl/cm$^2$), C2-80 denotes Comparative Example 1-2: DNase solution quantity 80 µl (208 µl/cm$^2$), C3 denotes Comparative Example 1-3: DNase solution quantity 0 µl, M denotes RNA molecular weight marker, 1 denotes Example 1-3, 2 denotes Comparative Example 1-5, 3 denotes Example 1-4: DNase solution quantity 10 µl (26 µl/cm$^2$), 4 denotes Comparative Example 1-6: DNase solution quantity 80 µl (208 µl/cm$^2$), M2 denotes a 1 kb PLUS Ladder, 5 denotes Example 1-5 Spleen of a Mouse: DNase solution quantity 10 µl (26 µl/cm$^2$), 6 denotes Comparative Example 1-7 Spleen of a Mouse: DNase Solution Quantity 80 µl (208 µl/cm$^2$), 7 denotes Example 1-6 Liver of a Mouse: DNase solution quantity 10 µl (26 µl/cm$^2$), 8 denotes Comparative Example 1-8 Liver of a Mouse: DNase solution quantity 80 µl (208 µl/cm$^2$), M3 denotes a 1 kb PLUS Ladder.

BEST MODE FOR CARRYING OUT THE INVENTION

A first method for selectively separating and purifying nucleic acid of the invention, using a cartridge for separation and purification of nucleic acid comprising a container having at least two openings wherein the cartridge for separation and purification of nucleic acid receives a nucleic acid-adsorbing porous membrane, which a mixture solution of nucleic acid containing DNA and RNA can pass through, in an inside of the container, comprising at least the steps of:

(1-a) adsorbing nucleic acid onto a nucleic acid-adsorbing porous membrane (hereinafter referred to as "adsorbing step");

(1-b) washing the nucleic acid-adsorbing porous membrane by using a washing solution, while the nucleic acid is adsorbed thereto (hereinafter referred to as "washing step 1");

(1-c) subjecting the nucleic acid-adsorbing porous membrane to a DNase treatment (reacting DNase in the nucleic acid-adsorbing porous membrane);

(1-d) washing the nucleic acid-adsorbing porous membrane by using a washing solution (hereinafter referred to as "washing step 2"); and (1-e) desorbing RNA from an inside of the nucleic acid-adsorbing porous membrane by using the recovering solution and discharging it out of the cartridge container (hereinafter referred to as "recovery step")

In each step of (1-a), (1-b), (1-c), (1-d) and (1-e), it is preferred to pass a mixture solution of nucleic acid containing DNA and RNA, a washing solution, a DNase solution or a recovering solution through a nucleic acid-adsorbing porous membrane in a pressurized condition; more preferably, a mixture solution of nucleic acid, a washing solution, a DNase solution or a recovering solution is injected to one opening of a cartridge for separation and purification of nucleic acid comprising a container having at least two openings wherein the cartridge for separation and purification of nucleic acid receives the nucleic acid-adsorbing porous membrane in an inside of the container, wherein a pressure difference-generating apparatus, which connects to the one opening of the cartridge, is used to make an inside of the cartridge for separation and purification of nucleic acid into a pressurized state, so as to each injected solutions is passed through and discharged from an another opening. It is preferred that a mixture solution of nucleic acid containing DNA and RNA, a washing solution, a DNase solution or a recovering solution is passed through aforementioned porous membrane under a pressurized state so that an apparatus can be compacted and automated. Pressurization by a pump is preferably in a range of 10 to 300 kPa, and more preferably in a range of 40 to 200 kPa.

More preferably, RNA can be separated and purified in the following steps, by using the cartridge for separation and purification of nucleic acid receiving the aforementioned nucleic acid-adsorbing porous membrane.

That is, (1-1) a step of injecting a mixture solution of nucleic acid containing DNA and RNA into one opening of a cartridge for separation and purification of nucleic acid comprising a container having at least two openings wherein the cartridge for separation and purification of nucleic acid receives the nucleic acid-adsorbing porous membrane, which the solutions can pass through, in an inside of the container, (1-2) a step of making an inside of the cartridge for separation and purification of nucleic acid into a pressurized state by using a pressure difference-generating apparatus connected to the one opening of the cartridge for separation and purification of nucleic acid, so as to pass the injected mixture solution of nucleic acid containing DNA and RNA through the nucleic acid-adsorbing porous membrane, and discharge the injected mixture solution of nucleic acid containing DNA and RNA from an another opening of the cartridge for separation and purification of nucleic acid, and thereby adsorbing nucleic acid to the nucleic acid-adsorbing porous membrane, (1-3) a step of injecting a washing solution into the one opening of the cartridge for separation and purification of nucleic acid, (1-4) a step of making the inside of the cartridge for separation and purification of nucleic acid into a pressurized state by using a pressure difference-generating apparatus connected to the one opening of the cartridge for separation and purification of nucleic acid, so as to pass the injected washing solution through the nucleic acid-adsorbing porous membrane and discharge the injected washing solution from an another opening, and thereby washing the nucleic acid-adsorbing porous membrane, while nucleic acid is adsorbed thereto, (1-5) a step of injecting a DNase solution into the one opening of the cartridge for separation and purification of nucleic acid, so as to subject the nucleic acid-adsorbing porous membrane to DNase treatment, (1-6) a step of making the inside of the cartridge for separation and purification of nucleic acid into a pressurized state by using a pressure difference-generating apparatus connected to the one opening of the cartridge for separation and purification of nucleic acid, so as to pass the injected DNase solution through the nucleic acid-adsorbing porous membrane and discharge the injected DNase solution from an another opening, (1-7) a step of injecting the washing solution into the one opening of the cartridge for separation and purification of nucleic acid, (1-8) a step of making the inside of the cartridge for separation and purification of nucleic acid into a pressurized state by using a pressure difference-generating apparatus connected to the one opening of the cartridge for separation and purification of nucleic acid, so as to pass the injected washing solution through the nucleic acid-adsorbing porous membrane and discharge the injected washing solution from an another opening, and thereby washing the nucleic acid-adsorbing porous membrane, while RNA is adsorbed thereto, (1-9) a step of injecting the recovering solution into the one opening of the cartridge for separation and purification of nucleic acid, and (1-10) a step of making the inside of the cartridge for separation and purification of nucleic acid into a pressurized state by using a pressure difference-generating apparatus connected to the one opening of the cartridge for separation and purification of nucleic acid, so as to pass the injected recovering solution through the nucleic acid-adsorbing porous membrane and discharge the injected recovering solution from an another opening, and thereby desorbing RNA from the nucleic acid-adsorbing porous membrane and discharging the desorbed RNA out of the cartridge for separation and purification of nucleic acid container.

In the aforementioned steps of separation and purification of RNA, it is possible to end the procedure from the first injection of a mixture solution of nucleic acid to the obtaining of RNA out of a cartridge for separation and purification of nucleic acid, within substantially less than 20 minutes, at a very adequate condition within less than 2 minutes.

In addition, in the aforementioned steps of separation and purification of RNA, RNA having a purity corresponding to an absorbance measurement of ultraviolet-visible spectrophotometer (260 nm/280 nm) of 1.8 to 2.2 can be recovered, and RNA of high purity with little amount of impurities contamination can be obtained for constant. At a very adequate condition, RNA having a purity corresponding to an absorbance measurement of ultraviolet-visible spectrophotometer (260 nm/280 nm) of around 2.0 can be recovered.

Further, a second method for separating and purifying nucleic acid comprises at least the steps of (2-a) adsorbing nucleic acid to a nucleic acid-adsorbing porous membrane by passing a mixture solution of nucleic acid containing RNA and DNA through the nucleic acid-adsorbing porous membrane, (2-b) washing the nucleic acid-adsorbing porous membrane by passing a washing solution through the nucleic acid-adsorbing porous membrane, while the nucleic acid is adsorbed thereto, and (2-c) desorbing the nucleic acid from the porous membrane by passing a recovering solution through the nucleic acid-adsorbing porous membrane.

In each of the steps of (2-a), (2-b) and (2-c), it is preferred to pass a mixture solution of nucleic acid containing DNA and RNA, a washing solution or a recovering solution through a nucleic acid-adsorbing porous membrane by using a pressure difference-generating apparatus. In each of the steps of (2-a), (2-b) and (2-c), it is more preferred to inject a sample solution containing nucleic acid, a washing solution or a recovering solution into one opening of a cartridge for separation and purification of nucleic acid comprising a container having at least two openings wherein the cartridge for separation and purification of nucleic acid receives the nucleic acid-adsorbing porous membrane in an inside of the container, and make an inside of the cartridge into a pressurized state by using a pressure difference-generating apparatus connected to the one opening of the cartridge, so as to pass each injected solutions through the nucleic acid-adsorbing porous membrane and discharge them from an another opening. It is preferred that a mixture solution of nucleic acid containing DNA and RNA, a washing solution or a recovering solution is passed through aforementioned porous membrane under a pressurized state so that an apparatus can be compacted and automated. Pressurization by a pump is preferably in a range of 10 to 300 kPa, and more preferably in a range of 40 to 200 kPa.

More preferably, RNA and DNA can be separated and purified in the following steps, by using the cartridge for separation and purification of nucleic acid receiving the aforementioned nucleic acid-adsorbing porous membrane.

That is, (2-1) a step of injecting a mixture solution of nucleic acid containing DNA and RNA into one opening of a cartridge for separation and purification of nucleic acid comprising a container having at least two openings wherein the cartridge for separation and purification of nucleic acid receives the nucleic acid-adsorbing porous membrane, which the solutions can pass through, in an inside of the container, (2-2) a step of making an inside of the cartridge for separation and purification of nucleic acid into a pressurized state by using a pressure difference-generating apparatus connected to the one opening of the cartridge for separation and purification, so as to pass the injected mixture solution of nucleic acid containing DNA and RNA through the nucleic acid-adsorbing porous membrane and discharge the injected mixture solution from an another opening of the cartridge for separation and purification of nucleic acid, and thereby adsorbing nucleic acid to the nucleic acid-adsorbing porous membrane, (2-3) injecting a washing solution into the one opening of the cartridge for separation and purification of nucleic acid, (2-4) making the inside of the cartridge for separation and purification of nucleic acid into a pressurized state by using a pressure difference-generating apparatus connected to the one opening of the cartridge for separation and purification of nucleic acid, so as to pass the injected washing solution through the nucleic acid-adsorbing porous membrane and discharge the injected washing solution from an another opening, and thereby washing the nucleic acid-adsorbing porous membrane, while the nucleic acid is adsorbed thereto, (2-5) injecting a recovering solution into the one opening of the cartridge for separation and purification of nucleic acid, and (2-6) making the inside of the cartridge for separation and purification of nucleic acid into a pressurized state by using a pressure difference-generating apparatus connected to the one opening of the cartridge for separation and purification of nucleic acid, so as to pass the injected recovering solution through the nucleic acid-adsorbing porous membrane and discharge the injected recovering solution from an another opening, and thereby desorbing nucleic acid from the nucleic acid-adsorbing porous membrane and discharging the desorbed nucleic acid out of the cartridge for separation and purification of nucleic acid container.

In the aforementioned steps of separation and purification of nucleic acid, it is possible to end the procedure from the first injection of a sample solution containing nucleic acid to the obtaining of nucleic acid out of a cartridge for separation and purification of nucleic acid, within substantially less than 20 minutes, at a very adequate condition within less than 2 minutes.

In addition, in the aforementioned steps of separation and purification of nucleic acid, nucleic acid in case of including DNA having a purity corresponding to an absorbance measurement of ultraviolet-visible spectrophotometer (260 nm/280 nm) of 1.6 to 2.0 and in case of including RNA having a purity corresponding to an absorbance measurement of ultraviolet-visible spectrophotometer (260 nm/280 nm) of 1.8 to 2.2 can be recovered, and nucleic acid of high purity with little amount of impurities contamination can be obtained for constant. Further, those having an absorbance measurement of ultraviolet-visible spectrophotometer (260 nm/280 nm) of around 1.8 for DNA and around 2.0 for RNA can be recovered.

In addition, in the aforementioned steps of both methods, examples of a pressure difference-generating apparatus include a pump and the like capable of increasing pressure such as a syringe, a pipette, a perista pump, or an evaporator and the like capable of decreasing pressure. Among these, a syringe and a pump are suitable for a hand-operation and for an automatic operation, respectively.

Additionally, a pipette has its merits for operating easily with one hand. Preferably, the pressure difference-generating apparatus is detachably connected to one opening of the cartridge for separation and purification of nucleic acid.

Further in the aforementioned steps of both methods, making an inside of the cartridge for separation and purification of nucleic acid into a depressurized state by using a pressure difference-generating apparatus connected to an another opening of the cartridge for separation and purification of nucleic acid can also be performed preferably. Further, centrifuging the cartridge for separation and purification of nucleic acid can also be performed preferably.

A Test Sample and a Mixture Solution of Nucleic Acid Containing DNA and RNA

A test sample to be used in the invention is not limited as long as a test sample contains nucleic acid, for examples thereof in the field of diagnostics include body fluids collected as test samples, such as whole blood, plasma, serum, urine, faeces, semen and saliva, or plants (or a part thereof), animals (or a part thereof), bacteria, virus, cultured cells, solutions prepared from biological materials such as lysates and homogenates of the above samples. The cultured cells include the floating-type cells and adhesive-type cells. The floating-type cells represent cells that float around within a culture solution for rearing and multiplication and not having to adhere onto the wall of a container, and for example, HL60, U937, HeLaS3, etc are exemplified as the representative cell strains. The adhesive-type cells represent cells that adhere onto the bottom surface of a container within a culture solution for rearing and multiplication, and for example, NIH3T3, HEK293, HeLa, COS, CHO, etc. are exemplified as the representative cell strains. An animal (or its portion) to be used as a test sample can be the tissue thereof. For example, all tissues obtained from dissection of an animal or biopsy, such as a liver, a kidney, a spleen, a brain, a heart, a lung or a thymus gland, composing a bion can be used.

These test samples are treated with an aqueous solution comprising a reagent which dissolves cell membranes and nuclear membrane, and solubilizes nucleic acid, so called a nucleic acid-solubilizing reagent. This enables cell membranes and nuclear membranes to be dissolved, and enables nucleic acid to be dispensed into the aqueous solution to obtain a mixture solution of nucleic acid.

It is preferred to obtain a mixture solution of nucleic acid by the following procedure:
(I) injecting a test sample into a container;
(II) adding a nucleic acid-solubilizing reagent to the container and thereby mixing the test sample with the nucleic acid-solubilizing reagent so as to obtain a mixture solution; and
(III) adding a water-soluble organic solvent to the above obtained mixture solution.

Examples of the nucleic acid-solubilizing reagent include at least one selected from a chaotropic salt, a nucleic acid stabilizing agent, a surfactant, a buffer and a defoaming agent.

As the chaotropic salt, known chaotropic salts can be used without any particular limitations. For example, guanidine salt, sodium isothiocyanate, sodium iodide and potassium iodide can be used. Especially, guanidine salt is preferred. Examples of guanidine salt include guanidine hydrochloride, guanidine isothiocyanate and guanidine thiocyanate salt (guanidine thiocyanate), and especially guanidine hydrochloride or guanidine thiocyanate salt is preferred. These salts can be used alone or in combinations of two or more.

The concentration of a chaotropic salt in the nucleic acid-solubilizing reagent is preferably 0.5 mol/L or more, more preferably from 0.5 to 8 mol/L and even more preferably from 1 to 6 mol/L.

It is possible to use a chaotropic substance such as urea instead of a chaotropic salt.

The nucleic acid-solubilizing reagent preferably comprises a nucleic acid stabilizing agent. It is preferred to use a nucleic acid stabilizing agent because a nucleic acid stabilizing agent cart stabilizes nucleic acid in a test sample. More preferably, any one or more selected from a chaotropic salt, a surfactant, a buffer and a defoaming agent is coexisted. By this mixing, a recovering yield and a recovering efficiency of finally obtained RNA are improved so that the minimization and acceleration of a test sample are enabled.

As the nucleic acid stabilizing agent, one having a reaction to inactivate a nuclease activity can be exemplified. Depending on a test sample, there are cases where nuclease, which degrades nucleic acid, is comprised thereto so that when nucleic acid is homogenized, nuclease reacts with nucleic acid, so as to result in a remarkable reduction of a yield amount. For the purpose of avoiding this, a stabilizing agent having a function to inactivate nuclease can be coexisted in a nucleic acid-solubilizing solution. As a result, improvements in a recovering yield and a recovering efficiency of nucleic acid lead to the minimization and acceleration of a test sample.

As the nucleic acid stabilizing agent having functions to inactivate the nuclease activity, a compound used routinely as a reducing agent can be used. Examples of reducing agents include hydrogenated compounds such as a hydrogen atom, hydrogen iodide, hydrogen sulfide, aluminum lithium hydride, and sodium borohydride; a highly electropositive metal such as alkaline metal, magnesium, calcium, aluminum, and zinc, or their amalgam; organic oxides such as aldehyde-based, sugar-based, formic acid, and oxalic acid; and mercapto compounds. Among these, the mercapto compounds are preferable. Examples of mercapto compounds include N-acetyl cysteine, mercapto ethanol, and alkyl mercaptane or the like. The mercapto compounds can be used alone or in combinations of two or more.

The concentration of the nucleic acid stabilizing agent in the nucleic acid-solubilizing reagent is preferably from 0.1 to 20% by weight, and more preferably from 0.3 to 15% by weight. The concentration of the mercapto compounds in the nucleic acid-solubilizing reagent is preferably from 0.1 to 20% by weight, and more preferably from 0.5 to 15% by weight.

Surfactants, for example, include a nonionic surfactant, a cationic surfactant, an anionic surfactant, an amphoteric surfactant.

In the invention, the nonionic surfactant and the cationic surfactant can be preferably used.

Nonionic surfactants include a polyoxyethylene alkyl phenyl ether-based surfactant, a polyoxyethylene alkyl ether-based surfactant, and fatty acid alkanolamide, and the preferable one is a polyoxyethylene alkyl ether-based surfactant. Among the polyoxyethylene (POE) alkyl ether surfactant, POE decyl ether, POE lauryl ether, POE tridecyl ether, POE alkylenedecyl ether, POE sorbitan monolaurate, POE sorbitan monooleate, POE sorbitan monostearate, tetraoleic polyoxyethylene sorbit, POE alkyl amine, and POE acetylene glycol are more preferred.

Cationic surfactants include cetyl trimethyl ammonium bromide, dodecyl trimethyl ammonium chloride, tetradecyl trimethyl ammonium chloride, cetyl pyridinium chloride.

These surfactants can be used alone or in combinations of two or more. The concentration of the surfactant in the nucleic acid-solubilizing reagent is preferably from 0.1 to 20% by weight.

The nucleic acid-solubilizing reagent having preferably pH of 3 to 8, more preferably pH of 4 to 7, and further preferably pH of 5 to 7, is used.

For a buffer, a normal pH buffer (buffer) can be used. Preferably, a biochemical pH buffer can be used. Examples of such buffers include buffers comprising citrate, phosphate or acetate, Tris-HCl, TE (Tris-HCl/EDTA), TBE (Tris-Borate/EDTA), TAE (Tris-Acetate/EDTA), and the GUD buffer. Examples of the GUD buffer include MES(2-Morpholinoethanesulfonic acid), Bis-Tris(Bis(2-hydroroxyethyl)iminotris (hydroxymethyl)methane), HEPES(2-[4-(2-Hydroxyethyl)-1-piperazinyl]ethanesulfonic acid), PIPES(Pipemxine-1,4-bis(2-ethanesulfonic acid)), ACES(N-(2-Acetamino)-2-aminoethanesulfonic acid), CAPS(N-Cyclohexyl-3-aminopropanesulfonic acid), TES(N-Tris(hydroxymethyl)methyl-2-aminoethanesulfonic acid).

The concentration of these buffers in the nucleic acid-solubilizing reagent for the first method is preferably in a range of 1 to 500 mmol/L. The concentration of these buffers in the nucleic acid-solubilizing reagent for the second method is also preferably in a range of 1 to 500 mmol/L.

As the defoaming agent, a silicon-based defoaming agent (e.g., silicon oil, dimethyl polysiloxane, silicon emersion, denatured polysiloxane, silicon compound, etc.), alcohol-based defoaming agent (e.g., acetylene glycol, heptanol, ethyl exanol, superhigh grade alcohol, polyoxy alkylene glycol, etc.), ether-based defoaming agent (e.g., heptyl cellosolve, nonyl cellosolve-3-heptylcorbitol, etc.), fatty oil-based defoaming agent (e.g., animal and plant fat, etc.), fatty acid-based defoaming agent (e.g., stearic acid, oleic acid, palmitic acid, etc.), metallic soap-based defoaming agent (e.g., aluminum stearate, calcium stearate, etc.), fatty acid ester-based defoaming agent (e.g., a natural wax, tributyl phosphate, etc.), phosphate ester-based defoaming agent (e.g., sodium octyl phosphate, etc.), amine-based defoaming agent (e.g., diamyl amine, etc.), amide-based defoaming agent (e.g., amide stearate, etc.), and other defoaming agents (e.g., ferric sulfate, bauxite, etc.) can be exemplified. These defoaming agent can be used alone or in combinations of two or more. Two compounds combined from silicon-based and alcohol-based defoaming agents are especially preferred.

The concentration of a defoaming agent in nucleic acid-solubilizing reagent is preferably in a range of 0.1 to 10% by weight.

In addition, the nucleic acid-solubilizing reagent may contain water-soluble organic solvent. Examples of water-soluble organic solvent include acetone, chloroform, alcohols and dimethylformamide. Preferably, its purpose is to increase the solubility of various reagents comprised in the nucleic acid-solubilizing reagent. Among these, alcohols are preferred. As for alcohols, any one of primary, secondary, tertiary alcohols can be used. More preferably, methanol, ethanol, propanol and its isomer, butanol and its isomer can be used. These water-soluble organic solvents can be used alone or in combinations of two or more. The concentration of these water-soluble organic solvents in the nucleic acid-solubilizing reagent is preferably in a range of 1 to 20% by weight.

It is preferred to homogenize the test sample before or after adding the nucleic acid-solubilizing reagent. Further, it is preferred to homogenize the solution obtained by adding the nucleic acid-solubilizing reagent. By homogenizing, automation aptitude preferably improves. Homogenizing can be treated by using, for example, a sonic treatment, a treatment using a sharp projection, a treatment using high-speed stirring, a treatment by pushing through fine voids, and a treatment using beads such as a glass, a stainless, and a zirconia.

There is not specific limitation to perform these treatments, for example, any of a mixer such as a vortex mixer, a homogenizer such as a Rotor-stator homogenizer, a Potter homogenizer and a Dounce homogenizer, a Bead-mill, a pestle, a French-press, a Grinder and a Blade homogenizer etc. can be used. When homogenizing before adding nucleic-acid solubilizing reagent, after place the test sample in liquid nitrogen, it is possible to grind or pulverize by using a mortar and a pestle, a bead-mill, crasher or pulverizer.

A method for mixing the homogenized analyte and the nucleic acid-solubilizing reagent is not especially limited hereto. For example, when mixing, using a stirrer or a mixer at 30 to 3000 rpm for 1 second to 3 minutes is preferred. By this mixing, the final yield of separated and purified RNA or nucleic acid can be increased very preferably. On the other hand, rollover-mixing for 5 to 30 times is also preferable. In addition, pipetting operation for 10 to 50 times enables blending, and in this case the final yield of RNA and nucleic acid separated and purified could increase in a simple operation, thereby preferred.

When the test sample is like a cultured cell or a yeast and so on, treating 50 to 1000 μl of nucleic-acid solubilizing reagent per 10 to $1 \times 10^8$ cells is preferred. When the test sample is like a tissue of animal or plant or something, treating 50 to 1000 μl of nucleic-acid solubilizing reagent per 0.1 to 200 mg of tissue is preferred. In the case of the test sample is a bacteria, treating 50 to 1000 μl nucleic-acid solubilizing reagent per 0.1 to 10 ml bacterial culture is preferred. The volume of the nucleic-acid solubilizing reagent can be changed under not to exceed the volume of the cartridge and to achieve complete lysis of the test sample.

Adding a water-soluble organic solvent additionally to the mixed solution obtained mixing a nucleic acid solubilizing reagent added to a test sample with the test sample is preferred. For the water-soluble organic solvent, an alcohol-based compound is preferably used, although not limited thereto. For alcohol-based compound, any one of primary, secondary, tertiary alcohols can be used, and methanol, ethanol, propanol and its isomer, butanol and its isomer can preferably be used. These water-soluble organic solvents can be used alone or in combinations of two or more. The final concentration of these water-soluble organic solvents in the nucleic acid-solubilizing reagent is preferably in a range of 5 to 90% by weight.

For example, when mixing after adding a water-soluble organic solvent, using an agitating apparatus at 30 to 3000 rpm for 1 second to 3 minutes is preferred. By this mixing, the final yield of separated and purified RNA or nucleic acid can be increased. And inverting the tube 5 to 30 times is also preferable. In addition, pipetting operation for 10 to 50 times enables blending, and in this case the final yield of RNA and nucleic acid separated and purified could increase in a simple operation, thereby preferred.

Additionally, obtained mixture solution of nucleic acid having surface tension of 0.05 J/m² or less, and having viscosity of 1 to 10000 mPa, further having specific gravity in a range of 0.8 to 1.2 is preferred. By using a solution fit in the range, removing the mixture solution of nucleic acid waste after passing the mixture solution of nucleic acid through a nucleic acid-adsorbing porous membrane is easily conducted (1-a) and (2-a) Step of Adsorbing Nucleic Acid onto a Nucleic Acid-Adsorbing Porous Membrane (Adsorption Step)

A nucleic acid-adsorbing porous membrane used in the present invention, and (1-a) and (2-a) a step of adsorbing nucleic acid onto a nucleic acid-adsorbing porous membrane are described below.

The nucleic acid-adsorbing porous membrane of the invention, which a solution can pass through internally, is used. Herein, "a solution can pass through internally" means that when a space contacting one side and a space contacting the other side of a membrane has a different pressure, a solution is enabled to pass through the membrane from the high pressured space to the low pressured space. On the other hand, it means that when the centrifuge force is applied to the membrane, a solution is enabled to pass through the membrane in the direction of the centrifuge force.

The nucleic acid-adsorbing porous membrane of the invention adsorbs nucleic acid by interaction therebetween, in which an ionic bond is not substantially involved. It means that "ionization" is not occurred under conditions of using a porous membrane, and it is assumed that nucleic acid and the porous membrane are attracting therebetween by changing the polarity in the surroundings. As a result, the nucleic acid-adsorbing porous membrane is preferably excellent in separation ability and good in washing efficiency, and preferably enables isolation and purification of nucleic acid. More preferably, the nucleic acid-adsorbing porous membrane is a porous membrane having a hydrophilic group, and it is assumed that the hydrophilic groups of nucleic acid and a porous membrane are attracting therebetween by changing the polarity in the surroundings.

Wherein, the hydrophilic group represents a polar group (an atomic group) which can have interaction therebetween with water, and all groups (atomic groups) related to adsorbing nucleic acid are suitable. For a hydrophilic group, the intensity of interaction therebetween with water having about intermediate intensity (refer to as the term "a hydrophilic group", wherein "a group which the hydrophilicity is not very strong", Dictionary of Chemistry, published by Kyoritsu Shuppan Co., Ltd.) is suitable. Examples include a hydroxyl group, a carboxyl group, a cyano group, and an oxyethylene group. A hydroxyl group is preferred.

Wherein, a porous membrane having a hydrophilic group means that the material itself for composing the porous membrane is having a hydrophilic group, or a hydrophilic group is introduced thereto by treating or coating the material which composes the porous membrane. Any one of organic or inorganic materials is suitable for the material composing the porous membrane. For example, the porous membrane, in which the material itself for composing the porous membrane is an organic material having a hydrophilic group; in which the hydrophilic group is introduced thereto by treating the organic material not having a hydrophilic group which composes the porous membrane; in which the hydrophilic group is introduced thereto by coating the organic material not having a hydrophilic group which composes the porous membrane; in which the material itself for composing the porous membrane is an inorganic material having a hydrophilic group; in which the hydrophilic group is introduced thereto by treating the inorganic material not having a hydrophilic group which composes the porous membrane; in which the hydrophilic group is introduced thereto by coating the inorganic material not having a hydrophilic group which composes the porous membrane is usable. However, for simplicity in stepping, using an organic material such as organic polymer for the material composing the porous membrane is preferred.

Examples of a material of a porous membrane having a hydrophilic group include polyhydroxy ethylacrylate, poly hydroxyl ethylmethacrylate, polyvinyl alcohol, polyvinyl pyrrolidone, polyacrylate, polymethacrylate, polyoxyethylene, acetyl cellulose, and a mixture of acetyl celluloses which are different in acetyl value from each other are suitable for composing the porous membrane, but particularly an porous membrane comprising organic material having a hydroxyl group, particularly the porous membrane comprising the organic polymer having a hydroxyl group can be used preferably.

For a porous membrane comprising organic material having a hydroxyl group, a material having polysaccharide structure is preferred, and a mixture of acetyl celluloses which are different in acetyl value from each other which compose an organic polymer porous membrane can be used more preferably. Examples of a mixture of acetyl celluloses which are different in acetyl value from each other include a mixture of triacetyl cellulose and diacetyl cellulose, a mixture of triacetyl cellulose and monoacetyl cellulose, a mixture of triacetyl cellulose, diacetyl cellulose and monoacetyl cellulose, a mixture of diacetyl cellulose and monoacetyl cellulose can be used preferably. Especially, a mixture of triacetyl cellulose and diacetyl cellulose can be used more preferably. Especially, the mixing ratio (mass ratio) of triacetyl cellulose and diacetyl cellulose is preferably 99:1 to 1:99, and more preferably 90:10 to 50:50.

More preferable organic material having a hydroxyl group is a saponification of acetyl cellulose disclosed in Japanese Patent Application Publication No. 2003-128691. Saponification of acetyl cellulose used herein means that a mixture of acetyl celluloses which are different in acetyl value from each other is treated with saponification, and examples including saponification of a mixture of triacetyl cellulose and diacetyl cellulose, a mixture of triacetyl cellulose and monoacetyl cellulose, a mixture of triacetyl cellulose, diacetyl cellulose and monoacetyl cellulose, and a mixture of diacetyl cellulose and monoacetyl cellulose can be used preferably. A special preference is given to a saponification of a mixture of triacetyl cellulose and diacetyl cellulose. The mixing ratio (mass ratio) of triacetyl cellulose and diacetyl cellulose is preferably 99:1 to 1:99, and more preferably 90:10 to 50:50. This allows the amount of hydroxyl group (density) on the surface of the porous membrane to be controlled according to the degree of surface saponification treatment (surface saponification degree).

In order to increase the efficacy of nucleic acid separation, having more amount (density) of the hydroxyl group on a surface of the porous membrane is preferred. The saponification degree of an organic material obtained from saponification is preferable in a range of 5 to 100%, and is more preferable in a range of 10 to 100%.

In addition, in order to enlarge the surface area of the organic polymers having a hydroxyl group on their surface, the treatment of surface saponification of acetyl cellulose is preferred.

A porous membrane having a front area and a back area symmetrical with each other is suitable, but a porous membrane having a front area and a back area asymmetrical with each other can be used preferably.

Herein, the saponification treatment means that acetyl cellulose comes in contact with saponification treatment solution (e.g., Sodium hydroxide solution). As a result, the saponification treatment solution contacted ester group of ester derivative of acetyl cellulose is hydrolyzed, and a hydroxyl group is introduced to form regenerated cellulose. Thereby the prepared regenerated cellulose is different in crystalline form from the original cellulose. In order to change the surface saponification degree, saponification treatment is conducted having changed the concentration or treating time of sodium hydroxide. The surface saponification degree is determined by means of NMR, IR or XPS (e.g., detecting a degree of reduction in the peak of carbonyl group).

A method for introducing a hydroxyl group to a porous membrane comprising organic material not having a hydroxyl group is to bond a graft polymer chain having a hydroxyl group in inner polymer strand or a side chain to a porous membrane. A method for bonding a graft polymer chain to an organic material of a porous membrane include two methods such as a method for chemically bonding a porous membrane with graft polymer chain, and a method for polymerizing a compound having a double bond capable of polymerization using a porous membrane as a starter to form graft polymer chain.

Firstly, in the method in which the porous membrane and graft polymer chain are chemically bonded, a polymer having a functional group capable of reacting with the porous membrane in the terminus or side chain of the polymer is used, and they are grafted through a chemical reaction of this functional group with a functional group of the porous membrane. The functional group capable of reacting with the porous membrane is not particularly limited with the proviso that it can react with a functional group of the porous membrane, and its examples include a silane coupling group such as alkoxysilane, isocyanate group, amino group, hydroxyl group, carboxyl group, sulfonate group, phosphate group, epoxy group, allyl group, methacryloyl group, acryloyl group and the like.

Examples of the compound particularly useful as the polymer having a reactive functional group in the terminus or side chain of the polymer include a polymer having trialkoxysilyl group in the polymer terminus, a polymer having amino group in the polymer terminus, a polymer having carboxyl group in the polymer terminus, a polymer having epoxy group in the polymer terminus and a polymer having isocyanate group in the polymer terminus. The polymer to be used in this case is not particularly limited with the proviso that it has a hydrophilic group which is concerned in the adsorption of nucleic acid, and its illustrative examples include polyhydroxyethyl acrylic acid, polyhydroxyethyl methacrylic acid and salts thereof, polyvinyl alcohol, polyvinyl pyrrolidone, polyacrylic acid, polymethacrylic acid and salts thereof, polyoxyethylene and the like.

The method in which a compound having a polymerizable double bond is made into a graft polymer chain by polymerizing it using the porous membrane as the starting point is generally called surface graft polymerization. The surface graft polymerization method means a method in which an active species is provided on the base material surface by plasma irradiation, light irradiation, heating or the like method, and a polymerizable compound having double bond arranged in contact with a porous membrane is linked to the porous membrane by polymerization.

It is necessary that the compound useful for forming a graft polymer chain linked to the base material has both of two characteristics of having a polymerizable double bond and having a hydrophilic group which is concerned in the adsorption of nucleic acid. As such a compound, any one of the polymers, oligomers and monomers having a hydrophilic group can be used with the proviso that it has a double bond in the molecule. Particularly useful compound is a monomer having a hydrophilic group.

As illustrative examples of the particularly useful monomer having a hydrophilic group, the following monomers can be cited. For example, 2-hydroxyethyl acrylate, 2-hydroxyethyl methacrylate, glycerol monomethacrylate and the like hydroxyl group-containing monomers can be used particularly suitably. In addition, acrylic acid, methacrylic acid and the like carboxyl group-containing monomers or alkali metal salts and amine salts thereof can also be used suitably.

As another method for introducing a hydrophilic group into a porous membrane of an organic material having no hydrophilic group, a material having a hydrophilic group can be coated. The material to be used in the coating is not particularly limited with the proviso that it has a hydrophilic group which is concerned in the adsorption of nucleic acid, but is preferably a polymer of an organic material from the viewpoint of easy handling. Examples of the polymer include polyhydroxyethyl acrylate, polyhydroxyethyl methacrylate and salts thereof, polyvinyl alcohol, polyvinyl pyrrolidone, polyacrylic acid, polymethacrylic acid and salts thereof, polyoxyethylene, acetyl cellulose, a mixture of acetyl celluloses having different acetyl values and the like, but a polymer having a polysaccharide structure is desirable.

Alternatively, it is possible to coat acetyl cellulose or a mixture of acetyl celluloses having different acetyl values on a porous membrane of an organic material having no hydrophilic group and then to subject the coated acetyl cellulose or a mixture of acetyl celluloses having different acetyl values to a saponification treatment. In that case, the saponification ratio is preferably about 5% or more and 100% or less. The saponification ratio is more preferably 10% or more and 100% or less.

As the porous membrane of an inorganic material having a hydrophilic group, a porous membrane containing a silica compound can be exemplified. As the porous membrane containing a silica compound, a glass filter can be exemplified. Also can be exemplified is a porous silica thin membrane described in Japanese Patent No. 3,058,3442. This porous silica thin membrane can be prepared by spreading a developing solution of a cationic amphipathic substance having an ability to form a bimolecular membrane on a base material, preparing multi-layered bimolecular thin membranes of the amphipathic substance by removing the solvent from the liquid membrane on the base material, allowing the multilayered bimolecular thin membranes to contact with a solution containing a silica compound, and then extracting and removing the aforementioned multi-layered bimolecular thin membranes.

Regarding the method for introducing a hydrophilic group into a porous membrane of an inorganic material having no hydrophilic group, there are a method in which the porous membrane and a graft polymer chain are chemically bonded and a method in which a graft polymer chain is polymerized using a hydrophilic group-containing monomer having a double bond in the molecule, using the porous membrane as the starting point.

When the porous membrane and graft polymer chain are attached by chemical bonding, a functional group capable of reacting with a terminal functional group of the graft polymer chain is introduced into an inorganic material, and the graft polymer chain is chemically bonded thereto. Also, when a graft polymer chain is polymerized using a hydrophilic group-containing monomer having a double bond in the molecule and using the porous membrane as the starting point, a functional group which becomes the starting point in polymerizing the double bond-containing compound is inserted into the inorganic material.

As the graft polymer having a hydrophilic group and hydrophilic group-containing monomer having a double bond in the molecule, the aforementioned graft polymer having a hydrophilic group and hydrophilic group-containing monomer having a double bond in the molecule, described in the foregoing regarding the method for introducing a hydrophilic group into a porous membrane of an organic material having no hydrophilic group, can be suitably use.

Another method for introducing a hydrophilic group to a porous membrane comprising inorganic material not having a hydrophilic group is to coat a material having a hydrophilic group thereon. Materials used in coating are not limited as long as the hydroxyl group participates in the adsorption of nucleic acid, but for easy workability, a polymer of organic material is preferred. Examples of polymer include polyhydroxyethylacrylate, polyhydroxyethylmethacrylate and their salts, polyvinyl alcohol, polyvinylpyrrolidone, polyacrylate, polymethacrylate and their salts, polyoxyethylene, acetyl cellulose, and a mixture of acetyl celluloses which are different in acetyl value from each other.

To the porous membrane comprising inorganic material not having a hydrophilic group, acetyl cellulose or a mixture of acetyl celluloses which are different in acetyl value from each other is coated thereon, and the coated acetyl cellulose and a mixture of acetyl celluloses which are different in acetyl value from each other can be saponified. In this case, the surface saponification degree in a range of 5% or more and 100% or less is preferred. It is more preferred to have the surface saponification degree in a range of 10% or more and 100% or less.

Examples of the porous membrane comprising inorganic material not having a hydrophilic group including aluminum and the like metals, glass, cement, pottery and the like ceramics, or a porous membrane fabricated by stepping new ceramics, silicon, active charcoal, etc.

The nucleic acid-adsorbing porous membrane is capable of passing a solution through the inside of the membrane, and having a thickness of 10 to 500 μm is preferred. It is more preferred to have the thickness in a range of 50 to 250 μm. It is preferable to have thinner thickness in the reason for easier washing.

The nucleic acid-adsorbing porous membrane capable of passing a solution through the inside of the membrane having the minimum pore size of 0.22 μm or more is preferred. Having the minimum pore size of 0.5 μm or more is more preferred. In addition, using a porous membrane having the ratio of the maximum pore size and the minimum pore size to be 2 or more is preferred. As a result, sufficient surface area for adsorbing nucleic acid can be obtained, and the pores are not clogged easily. More preferable ratio of the maximum pore size and the minimum pore size is 5 or more.

The nucleic acid-adsorbing porous membrane capable of passing a solution through the inside of the membrane having the percentage of porosity in a range of 50 to 95% is preferred. More preferable percentage of porosity is in a range of 65 to 80%. Further, having a bubble point in a range of 0.1 to 10 kgf/cm$^2$ is preferred. More preferable bubble point is in a range of 0.2 to 4 kgf/cm$^2$.

The nucleic acid-adsorbing porous membrane capable of passing a solution through the inside of the membrane having a pressure loss in a range of 0.1 to 100 kPa is preferred. As a result, a uniformed pressure can be obtained at pressurized states. More preferable pressure loss is in a range of 0.5 to 50 kPa. Herein, the term "pressure loss" represents the minimum pressure necessary for passing water through per 100 μm thickness of a membrane.

The nucleic acid-adsorbing porous membrane capable of passing a solution through the inside of the membrane having an amount of water percolation, at the time of passing water through under 1 kg/cm$^2$ pressure at 25° C., in a range of 1 to 5000 mL per 1 cm$^2$ membrane for 1 minute is preferred. More preferable amount of water percolation, at the time of passing water through under 1 kg/cm$^2$ pressure at 25° C., is in a range of 5 to 1000 mL per 1 cm$^2$ membrane for 1 minute.

The nucleic acid-adsorbing porous membrane capable of passing a solution through the inside of the membrane having an amount of nucleic acid-adsorption of 0.1 μg or more per 1 mg of a porous membrane is preferred. More preferable amount of nucleic acid-adsorption is 0.9 μg or more per 1 mg of a porous membrane.

The nucleic acid-adsorbing porous membrane capable of passing a solution through the inside of the membrane having a cellulose derivative, which does not dissolve in less than 1 hour, but dissolves in less than 48 hours when a square porous membrane having a side length of 5 mm is deposited in 5 mL of trifluoroacetic acid is preferred. Further, a cellulose derivative, which dissolves in less than 1 hour when a square porous membrane having a side length of 5 mm is deposited in 5 mL of trifluoroacetic acid, but does not dissolve in less than 24 hours when deposited in 5 mL of dichloromethane is preferred. Among them, a cellulose derivative, which dissolves in less than 1 hour when a square porous membrane having a side length of 5 mm is deposited in 5 mL of trifluoroacetic acid, but does not dissolve in less than 24 hours when deposited in 5 mL of dichloromethane is more preferred.

When passing a nucleic acid mixture solution through a nucleic acid-adsorbing porous membrane, it is preferred that passing the nucleic acid mixture solution from one side to another side allows the solution to uniformly contact with the porous membrane. When passing a nucleic acid mixture solution through a nucleic acid-adsorbing porous membrane, it is preferred that passing the nucleic acid mixture solution through the nucleic acid-adsorbing porous membrane from a bigger pore size to a smaller pore size in the purpose of not clogging the pore easily.

When passing a nucleic acid mixture solution through a nucleic acid-adsorbing porous membrane, it is preferred to have the flow rate in a range of 2 to 1500 μL/sec per unit area cm$^2$ of the membrane to obtain suitable contact time of the solution to the porous membrane. When the contact time of the solution to the porous membrane is too short, sufficient separation and purification effect cannot be obtained, and when too long, it is not preferred due to its operability. The flow rate in a range of 5 to 700 μL/sec per unit area cm$^2$ of the membrane is preferred.

In addition, the nucleic acid-adsorbing porous membrane capable of passing a solution through the inside of the membrane can be used in one layer, but also can be used in multi-layers. The multi-layers of the nucleic acid-adsorbing porous membrane can be identical to or different from each other.

The multi-layers of the nucleic acid-adsorbing porous membrane can have combination of inorganic material and organic material of the nucleic acid-adsorbing porous membrane. For example, a combination of a glass filter and regenerated cellulose of a porous membrane is possible. Further, the multi-layers of the nucleic acid-adsorbing porous membrane can have combination of inorganic material and organic material of the nucleic acid-adsorbing porous membrane. For example, a combination of a glass filter and nylon, or polysulfone, is possible.

A cartridge for separation and purification of nucleic acid comprising a container having at least two openings wherein the cartridge for separation and purification of nucleic acid receives the nucleic acid-adsorbing porous membrane, which solutions as mentioned above can pass through, in an inside of the container, can be used preferably. Further, a cartridge for separation and purification of nucleic acid comprising a container having at least two openings wherein the cartridge for separation and purification of nucleic acid receives the multi-layered nucleic acid-adsorbing porous membrane, which solutions as mentioned above can pass through, in an inside of the container, can be used preferably. In this case, the container which has at least two openings and receives the multi-layered nucleic acid-adsorbing porous membrane can be identical to or different from each other.

The cartridge for separation and purification of nucleic acid should not comprise other members except for comprising a container having at least two openings wherein the cartridge for separation and purification of nucleic acid receives the nucleic acid-adsorbing porous membrane, which solutions can pass through as mentioned above, in an inside of the container. Examples of materials for the container include plastics such as polypropylene, polystyrene, polycarbonate and polyvinyl chloride can be used. In addition, a biodegradable material can also be used preferably. Further, the container can be transparent or colored.

The cartridge for separation and purification of nucleic acid comprising the means for distinguishing between each cartridge for separation and purification of nucleic acid can be used. The means for distinguishing between each cartridge for separation and purification of nucleic acid may include a bar code, a 2-dementional bar code, a magnetic tape, and an IC card.

In addition, the cartridge for separation and purification of nucleic acid comprising a structure in which the nucleic acid-adsorbing porous membrane can be easily taken out from a container having at least two openings can be used.

(1-b) and (2-b) Step of Washing the Nucleic Acid-Adsorbing Porous Membrane by Using a Washing Solution, while Nucleic Acid is Adsorbed Thereto (1-b) and (2-b) A step of washing the nucleic acid-adsorbing porous membrane by using a washing solution, while nucleic acid is adsorbed thereto is described in the following.

Firstly the washing step (1-b) in the first method of the present invention is described below. By the washing step, the recovering yield and purity of finally obtained RNA is improved, and the amount of a test sample containing the necessary RNA is minimized. Further, by automating the step of washing and recovering, the step can be simple and rapidly conducted. For the acceleration, the washing step may be completed by washing once, and if its purity is more important, several times of washing are preferred In the washing step, a washing solution is provided to a cartridge for separation and purification of nucleic acid receiving the nucleic acid-adsorbing porous membrane by using a tube, a pipette, an automatic injection apparatus, or a providing means having the like function. The washing solution is provided from one opening of the cartridge for separation and purification of nucleic acid (the one opening where a nucleic acid mixture solution containing nucleic acid is injected), and a pressure difference-generating apparatus connecting to the one opening (e.g., a dropper, a syringe, a pump, a power pipette etc.) is used. Thereby making an inside of the cartridge for separation and purification of nucleic acid into a pressurized state, so as to pass the washing solution through the nucleic acid-adsorbing porous membrane, and discharge the washing solution from another opening different from the one opening. Additionally, the washing solution can be provided into one opening and discharged from the same opening. Further, the washing solution can be provided to another opening different from the one opening which the nucleic acid mixture solution containing nucleic acid is provided to, and discharged from the same opening. Among them, providing into one opening of the cartridge for separation and purification of nucleic acid, passing through nucleic acid-adsorbing porous membrane and discharging from another opening different from the one opening is much preferred due to its excellent washing efficiency.

In a washing procedure, the amount of a washing solution is preferably 2 µl/mm$^2$ or more. When large quantity of the washing solution is used, the washing effect could improve, but in order to maintain the operationability and prohibit the sample from discharging, 200 µl/mm$^2$ or less is preferred.

In a washing procedure, when passing a washing solution through a nucleic acid-adsorbing porous membrane, it is preferred to have the flow rate in a range of 2 to 1500 µl/sec per unit area (cm$^2$) of the membrane, and more preferably in a range of 5 to 700 µl/sec. Normally, the passing speed is reduced to elongate the time so that washing is sufficiently conducted. However, preferably, by using the aforementioned range in the invention the step for separating and purifying RNA can be conducted rapidly without reducing the washing efficiency.

In the washing step, a temperature of the washing solution in a range of 4 to 70° C. is preferred. Further, a temperature of the washing solution at room temperature is more preferred. In addition to the washing step, stirring using an ultrasonic or a mechanical vibration can be applied to the cartridge for separation and purification of nucleic acid at the same time. On the other hand, washing can be done by conducting a centrifugation.

In the washing step, the washing solution is a solution containing at least one of water-soluble organic solutions and water-soluble salts is preferred. It is necessary for a washing solution to have ability that works to wash out impurities of the nucleic acid mixture solution, which are adsorbed onto the nucleic acid-adsorbing porous membrane along with nucleic acid. In this regard, the washing solution must have such a composition that it desorbs only impurities from the nucleic acid-adsorbing porous membrane, and not the nucleic acid. In the purpose, nucleic acid are very insoluble to water-soluble organic solvents such as alcohol, therefore the water-soluble organic solvent is suitable for desorbing other substances by maintaining nucleic acid. In addition, adding water-soluble salts enables to increase an adsorption effect of nucleic acid, thereby improving the selectively removing operation for impurities and unnecessary substances.

For the water-soluble organic solvent, which is contained in a washing solution, alcohols can be used. Examples of alcohol include methanol, ethanol, isopropanol, n-isopropanol, and butanol. Any one of isopropanol and n-propanol is suitable for propanol, and any one of straight chained or branched is suitable for butanol. These alcohols can be used in two of more. Among these, ethanol is preferable.

The amount of water-soluble organic solvent in the washing solution in a range of 1 to 100% by weight is preferred, and more preferably in a range of 5 to 40% by weight. In this range, DNA contamination did not increase and RNA of interest did not desorb from the porous membrane, therefore preferably high purity and high yield of RNA was obtainable.

While for the water-soluble salt, salt of halide is preferred, and among these, chloride is preferred. Further, water-soluble salt having a monovalent or divalent cation is preferred, especially, alkaline metal and alkaline earth metal is preferred, among these, sodium salt, potassium salt and lithium salt is preferred, and sodium salt is most preferred.

When water-soluble salt is included in a washing solution, a concentration thereof is preferably 10 mmol/L or more, and as long as its maximum amount does not affect solubility of the impurities, the concentration in a range of 0.1 to 1 mol/L is preferred, although not limited. Above all, a concentration of sodium chloride of 20 mmol/L or more is preferred.

The washing solution is characterized in that a chaotropic substance is not comprised therein. As a result, a possibility of having a chaotropic substance mixed into a recovering procedure (1-e) can be decreased. In the case, where the chaotropic substance is mixed thereto, it sometime hinders enzyme reaction of a RT-PCR reaction or the like, therefore considering the afterward enzyme reaction, not including the chaotropic substance in a washing solution is ideal. Further, a chaotropic substance is corrosive and harmful, in view of this, it is extremely advantageous for the researcher not to be required to use chaotropic substance in terms of security.

Herein, the chaotropic substance represents aforementioned urea, guanidine chloride, guanidine isothiocyanate, guanidine thiocyanate, sodium isothiocyanate, sodium iodide, potassium iodide, etc.

Secondly, the washing step (2-b) in the second method of the present invention is described below.

According to the present invention, a washing solution is passed through the nucleic acid-adsorbing porous membrane, whereby DNA is eluted, and only RNA is adsorbed thereto, thereby allowing a small amount of a test sample containing necessary nucleic acid. That is, when the washing solution is dropped onto the porous membrane, DNA can be separated.

The washing solution of the invention is an aqueous solution which contains a water-soluble organic solvent having a concentration of 50% by weight or less, and preferably in a range of 1 to 50% by weight. It is necessary to have ability that works to wash out impurities of a sample solution, which are adsorbed onto the nucleic acid-adsorbing porous membrane along with nucleic acid. In this regard, it must have such a composition that it desorbs only impurities from the nucleic acid-adsorbing porous membrane, and not the nucleic acid.

In the case where the proportion of the water-soluble organic solvent in the washing solution is too high, DNA cannot be eluted in the washing step. Therefore, DNA contamination in a RNA solution recovered from the recovering solution is increased. Further, in the case where it is too low in the washing step, not only DNA but also RNA is desorbed from the porous membrane, which lowers the amount of RNA contained in the recovering solution. In this regard, the proportion of the water-soluble organic solvent in the washing solution is 50% by weight or less, and preferably in a range of 5 to 40% by weight.

For example, the water-soluble organic solvent, which is contained in the washing solution, includes alcohols such as methanol, ethanol, isopropanol, n-isopropanol, and butanol. Among these, ethanol is preferable.

The washing solution of the invention also preferably contains a water-soluble salt. For the water-soluble salt, a salt such halide is preferred, and among these, chloride is preferred. Further, the water-soluble salt having a monovalent or divalent cation is preferred, especially, an alkali metal salt and an alkaline earth metal salt are preferred and among these, a sodium salt, a lithium salt and a potassium salt are preferred, and the sodium salt is most preferred.

When the water-soluble salt is contained in a washing solution, a concentration thereof is preferably 10 mmol/L or more, and as long as the upper limit does not affect solubility of the impurities a concentration thereof is preferably 1 mol/L or less and more preferably 0.1 mol/L, although not particularly limited. More preferably, the water-soluble salt is sodium chloride, it contains 20 mmol/L or more of sodium chloride In addition, the washing solution is characterized in that a chaotropic substance is not contained therein. As a result, a possibility of having the chaotropic substance incorporated into a recovery step (2-c) after the washing step can be reduced. In the recovery step, where the chaotropic substance is incorporated thereinto, it sometimes hinders an enzyme reaction such a PCR reaction or the like, therefore considering the afterward enzyme reaction, not including the chaotropic substance to a washing solution is ideal. Further, the chaotropic substance is corrosive and harmful, in this regard, it is extremely advantageous from an operational safety standpoint for the researcher not to use the chaotropic substance when unnecessary. Since washing solution does not contain the chaotropic substance, RNA or nucleic acid having a purity corresponding to an absorbance measurement of ultraviolet-visible spectrometer (260 nm/230 nm) of more the 1.5 can be recovered. Further those having an absorbance measurement of ultraviolet-visible spectrometer (260 nm/230 nm) of around 2.0 of RNA or nucleic acid can be recovered.

Herein, the chaotropic substance represents aforementioned urea, guanidine chloride, guanidine isothiocyanate, guanidine thiocyanate, sodium isothiocyanate, sodium iodide, potassium iodide, etc.

In the washing step, a washing solution is provided to a cartridge for separation and purification of nucleic acid receiving the nucleic acid-adsorbing porous membrane by using a tube, a pipette, an automatic injection apparatus, or a providing means having the like function. The washing solution is provided from one opening of the cartridge for separation and purification of nucleic acid (the one opening where a nucleic acid mixture solution containing nucleic acid is injected), and a pressure difference-generating apparatus connecting to the one opening (e.g., a dropper, a syringe, a pump, a power pipette etc.) is used. Thereby making an inside of the cartridge for separation and purification of nucleic acid into a pressurized state, so as to pass the washing solution through the nucleic acid-adsorbing porous membrane, and discharge the washing solution from another opening different from the one opening. Additionally, the washing solution can be provided into one opening and discharged from the same opening. Further, the washing solution can be provided to another opening different from the one opening which the nucleic acid mixture solution containing nucleic acid is provided to, and discharged from the same opening. Among them, providing into one opening of the cartridge for separation and purification of nucleic acid, passing through nucleic acid-adsorbing porous membrane and discharging from another opening different from the one opening is much preferred due to its excellent washing efficiency.

In the washing step, the amount of the washing solution is preferably 2 μl/mm$^2$ or more. When a large quantity of the washing solution is used, the washing effect could improve, but in order to maintain the operationability and prohibit the sample from discharging, 200 μl/mm$^2$ or less is preferred.

In a washing procedure, when passing a washing solution through a nucleic acid-adsorbing porous membrane, it is preferred to have the flow rate in a range of 2 to 1500 μl/sec per unit area ($cm^2$) of the membrane, and more preferably in a range of 5 to 700 μl/sec. When it decreases the speed at passing the washing solution through the nucleic acid-adsorbing porous membrane, washing is sufficiently performed, but it is important to accelerate the operation for separating and purifying nucleic acid and thus the aforementioned ranges are selected.

In the washing step, a temperature of the washing solution in a range of 4 to 70° C. is preferred. Further, a temperature of the washing solution at room temperature is more preferred. Further, in the washing step, the washing can also be performed with stirring the cartridge by a mechanical vibration and an ultrasonic wave, or with a centrifugation.

Since the washing solution has high wettability for a cartridge or the like container, the washing solution sometimes remains in the container during the washing step in the nucleic acid separation purification process, so that the recovery step after the washing step is contaminated with the washing solution to cause reduction of the purity of nucleic acid and reduction of the reactivity in the subsequent step. Thus, in the first method and the second method of the present invention, when adsorption and desorption of nucleic acid are carried out using a cartridge or the like container, it is important that a solution to be used in the adsorption or washing, particularly the washing solution, does not remain in the cartridge so that it does not exert influence upon the next step.

Accordingly, in order to prevent contamination of the recovering solution of the subsequent step with the washing solution of the washing step and thereby to keep residue of the washing solution in the cartridge to the minimum, it is desirable that surface tension of the washing solution is less than 0.035 $J/m^2$. When the surface tension is low, wettability of the washing solution for the cartridge is improved and volume of the residual solution can be controlled.

However, the ratio of water can be increased in order to increase the washing efficiency, but in that case, surface tension of the washing solution is increased and amount of the residual solution is increased. When surface tension of the washing solution is 0.035 $J/m^2$ or more, amount of the residual solution can be controlled by increasing water repellency of the cartridge. By increasing water repellency of the cartridge, droplets are formed, and amount of the residual solution can be controlled by flow down of the droplets. Examples of the method for increasing water repellency include coating of a water repellant such as silicon on the cartridge surface, kneading of a water repellant such as silicon at the time of the cartridge forming, and the like, though not limited thereto.

In addition, by automatizing a washing and a recovering procedures, the operation can be conducted easier and faster. For the acceleration, the washing step may be completed by washing once, and if its purity is more important, several times of washing are preferred The washing step in the first method and the second method of the present invention can be simplified making use of the nucleic acid adsorbing porous membrane of the invention. (1) Frequency of the washing solution passing through the nucleic acid adsorbing porous membrane may be reduced to once. (2) The washing step can be carried out at room temperature. (3) After the washing, the recovering solution can also be immediately injected into the cartridge. (4) It is possible also to combine one or two or more of the aforementioned (1), (2) and (3). In the related methods, a drying step was frequently required in order to quickly remove an organic solvent contained in the washing solution, but the nucleic acid adsorbing porous membrane to be used in the invention is a thin membrane so that the drying step can be omitted.

In the related RNA and nucleic acid separation purification methods, there is a problem in that the washing is frequently scattered and adhered to other parts while carrying out the washing step to cause contamination (pollution) of samples. Such a type of contamination in the washing step can be inhibited by devising shapes of the cartridge for separation and purification of nucleic acid in which the nucleic acid adsorbing porous membrane is received in a container having two openings and of the waste water container.

(1-c) Step of Subjecting the Nucleic Acid-Adsorbing Porous Membrane to DNase Treatment (1-c) A step of subjecting the nucleic acid-adsorbing porous membrane to DNase treatment (a step of reacting DNase in the nucleic acid-adsorbing porous membrane) is described in the following. In order to selectively separating and purifying RNA from a nucleic acid mixture solution containing DNA and RNA, the mixture solution is passed through a cartridge for separation and purification of nucleic acid receiving a nucleic acid-adsorbing porous membrane, where nucleic acid is adsorbed thereto (adsorbing step), followed by performing washing (washing step 1), and a step of subjecting to DNase treatment is performed.

DNase is not particularly limited, and any DNase can be used. For example, pancreatic DNase I from animal like bovine, recombinant or synthetic DNase can be used.

For DNase solution (hereinafter it is also called DNase reacting solution) in case of subjecting to DNase treatment, divalent cation such as $Mg^{2+}$, $Ca^{2+}$, $Mn^{2+}$ suitable to make DNase activate may be added. And to keep RNA or nucleic acid adsorbed on nucleic-acid adsorbing porous membrane, monovalent cation such as $Na^+$, $Li^+$, $K^+$ can be coexisted. Also, to adjust pH for DNase reaction, adding normal buffer is preferred. Example for such buffers include Tris-HCl, HEPES(2-[4-(2-Hydroxyethyl)-1-piperazinyl]ethane-sulfonic acid), phosphate, borate, citrate.

In the method of the present invention, a step of subjecting the nucleic acid-adsorbing porous membrane received in a cartridge for separation and purification of nucleic acid to DNase treatment is conducted in an amount of total DNase solution of 130 μl or less per 1 $cm^2$ of the nucleic acid-adsorbing porous membrane. Commercially available, for example, RNeasy Mini Kit manufactured by Qiagen Inc. requires 80 μl of DNase solution (208 μl per 1 $cm^2$ of the nucleic acid-adsorbing porous membrane). Therefore, the invention can conduct a purification more cost effectively. Further, in the step of subjecting the nucleic acid-adsorbing porous membrane received in a cartridge for separation and purification of nucleic acid to DNase treatment, having the concentration of DNase in a range of 10 Kunitz U/mL or more and 10000 Kunitz U/mL or less is preferred, and 50 Kunitz U/mL or more and 5000 Kunitz U/mL or less is more preferred. In addition, herein used active Kunitz U is defined as "1 Kunitz U means a DNase activity that increase an absorbance of $A_{260}$ by 0.001 in 1 ml of reaction solution per one minute under the condition of using DNA as substrate at 25° C. in pH 5.0". Further, in the step of subjecting the nucleic acid-adsorbing porous membrane of a cartridge for separation and purification of nucleic acid to DNase treatment, having a time in a range of from 5 seconds to 360 minutes is preferred, although it depends on the amount of DNA in the nucleic acid mixture solution containing DNA and RNA, and the concentration of treating DNase, and more preferable in a range of from 30 seconds to 180 minutes. Further, in the step of subjecting the nucleic acid-adsorbing porous membrane of a cartridge for separation and purification of nucleic acid to DNase treatment, having a temperature at 4° C. or more is suitable, and a temperature in a range of from 10 to 50° C. is preferred, and having a high temperature, for example, of from 50 to 70° C. to enhance a reaction efficiency is possible. In addition, the expression "acting DNase in the nucleic acid-adsorbing porous membrane" means that DNase is reacted with the portion where nucleic acid is adsorbed to in the nucleic acid-adsorbing porous membrane, and the expression "in the nucleic acid-adsorbing porous membrane" is not limited only to on the nucleic acid-adsorbing porous membrane, but also in the pores of the porous membrane or the exit of the pores in the backside of the membrane or the like is comprised thereto.

(1-d) Step of Washing the Nucleic Acid-Adsorbing Porous Membrane by Using a Washing Solution (Washing Step 2)

(1-d) A step of washing the nucleic acid-adsorbing porous membrane by using a washing solution is performed after performing the step (1-c). The step (1-d) is performed in accordance with the step (1-b). Once or more of step (1-d) is performed.

(1-e) Step of Desorbing RNA from the Nucleic Acid-Adsorbing Porous Membrane by Using the Recovering Solution, and Discharging RNA out of the Cartridge Container (Recovery Step)

(1-e) The procedure of recovering RNA by desorbing from the nucleic acid-adsorbing porous membrane is described in the following.

In the recovering procedure, the recovering solution is provided to the cartridge for separation and purification of nucleic acid, which receives the nucleic acid-adsorbing porous membrane, by using a tube, a pipette, an automatic injection unit, or a providing means having the like function. The recovering solution is provided from one opening of the cartridge for separation and purification of nucleic acid (the one opening where a nucleic acid mixture solution containing nucleic acid is injected), and a pressure difference generating apparatus connecting to the one opening (e.g., a dropper, a syringe, a pump, a power pipette etc.) is used, thereby making an inside of the cartridge for separation and purification of nucleic acid into a pressurized state, so as to pass the recovering solution through the nucleic acid-adsorbing porous membrane, and discharge the recovering solution from another opening different from the one opening. Additionally, the recovering solution can be provided into one opening and discharged from the same opening. Further, the recovering solution can be provided to another opening different from the one opening which the nucleic acid mixture solution containing nucleic acid is provided to, and discharged from the same opening. Among them, providing into one opening of the cartridge for separation and purification of nucleic acid, passing through nucleic acid-adsorbing porous membrane and discharging from another opening different from the one opening is much preferred due to its excellent recovering efficiency.

Considering the volume of the nucleic acid mixture solution prepared from the test sample, the desorption of RNA can be conducted by controlling the volume of the recovering solution. The amount of the recovering solution containing separated and purified nucleic acid is related to the amount of a test sample used at the time. In general, the amount of the recovering solution commonly used is from several 10 µl to several 100 µl, but either extremely small quantity of a test sample is used or on the other hand a large amount of RNA is desired to be separated and purified, the amount of the recovering solution can be changed in a rage of 1 µl to several 10 ml.

For the recovering solution, purified distilled water, Tris/EDTA buffer and the like can preferably be used. Further, when providing the recovered nucleic acid to RT-PCR (Reverse Transcription Polymerase Chain Reaction), the buffer solution (e.g., an aqueous solution having the final concentration of 75 mmol/L of KCl, 50 mmol/L of Tris-HCl, 3.0 mmol/L of $MgCl_2$, 10 mmol/L of DDT) for RT-PCR can be used.

The pH of the recovering solution is preferably from pH 1 to 10, more preferably from pH 2 to 7. Especially, ion strength and the salt concentration have effects on the elution of adsorbed RNA. The recovering solution having 500 mmol/L of ion strength is preferred. Having 0.5 mol/L or less of salt concentration is preferred, and having 0.01 to 50 mmol/L of salt concentration is more preferred. Thereby, the yield of RNA increases, and a larger amount of RNA can be recovered.

A recovering solution containing concentrated nucleic acid can be obtained by reducing volume of the recovering solution in comparison with the volume of the original sample solution containing nucleic acid. Preferably, (volume of recovering solution):(volume of sample solution)=from 1:100 to 99:100, and more preferably, (volume of recovering solution):(volume of sample solution)=from 1:10 to 9:10. By this, RNA can be conveniently concentration without carrying out an operation for concentration at the after-step of the nucleic acid separation purification. By these methods, a method for obtaining RNA solution in which RNA is concentrated than the test sample can be provided.

In addition, as another aspect, a recovering solution containing a desired concentration of RNA can be obtained, and a recovering solution containing a concentration of RNA suited for the next step (For example, RT-PCR or the like) can be obtained, by carrying out desorption of RNA under such a condition that volume of the recovering solution becomes larger than the volume of the original sample solution containing nucleic acid. Preferably, (volume of recovering solution):(volume of sample solution)=from 1:1 to 50:1, and more preferably, (volume of recovering solution):(volume of sample solution)=from 1:1 to 5:1. By this, a merit, namely avoidance of the troublesome concentration adjustment after the separation and purification of nucleic acid, can be obtained. In addition, increase of RNA recovery ratio from the porous membrane can be made by the use of sufficient amount of the recovering solution.

Also, RNA can be conveniently recovered by changing temperature of the recovering solution in response to the purpose. For example, RNA solution can be obtained conveniently and efficiently, by preventing degradation of RNA through the inhibition of the action of ribonuclease without adding a certain reagent or a special operation capable of inhibiting enzymatic degradation, by carrying out desorption of RNA from the porous membrane after changing temperature of the recovering solution from 0 to 10° C.

Also, when temperature of the recovering solution is set to 10 to 35° C., recovery of RNA at general room temperature can be carried out and the RNA can be separated and purified by desorbing it without requiring a complex step.

In addition, as another aspect, desorption of RNA from the porous membrane can be carried out conveniently with high recovery ratio without mediating a complicated operation, by shifting temperature of the recovering solution to a high temperature of, for example, from 35 to 70° C.

The number of times of injection of the recovering solution is not limited, and it may be once or two or more times. In general, this is carried out by single recovery when RNA is separated and purified quickly and conveniently, but when a large amount of RNA is recovered, the recovering solution may be injected two or more times in some cases.

In the recovery step, it is possible to make the recovering solution of RNA into a composition which can be used in the after-step thereafter. The separated and purified RNA is sometimes applied to the RT-PCR (reverse transcription polymerase chain reaction) method. In that case, the separated and purified RNA solution must be diluted with a buffer solution suited for the RT-PCR method. By using a buffer solution suited for the RT-PCR method in the recovery step by this method, it can be shifted to the subsequent RT-PCR step conveniently and quickly.

Also, in the recovering step, it is possible to add a stabilizing agent for preventing degradation of RNA recovered in the recovering solution of RNA. As the stabilizing agent, an antibacterial agent, a fungicide, a nucleic acid degradation inhibitor and the like can be added. As the nuclease inhibitor, EDTA and the like can be cited. In addition, as another embodiment, a stabilizer can also be added to the recovery container in advance.

Also, the recovery container to be used in the recovery step is not particularly limited, a recovery container prepared from a raw material having no absorption at 260 nm can be used. In that case, concentration of the recovered RNA solution can be measured without transferring it into other container. As the raw material having no absorption at 260 nm, quartz glass and the like can for example be used, though not limited thereto.

The cartridge for separation and purification of nucleic acid used in aforementioned method for selectively separating and purifying RNA and the reagent used in each step of (1-a) to (1-e) can be used as a kit.

As disclosed above, for the method for separating and purifying RNA from a test sample containing nucleic acid by using a cartridge for separation and purification of nucleic acid receiving the nucleic acid-adsorbing porous membrane in a container having at least two openings and a pressure difference-generating apparatus, wherein the method can be conducted by using an automated apparatus which proceeds the steps automatically comprised in the method. In addition, the method can be conducted by using an automated apparatus which proceeds the use of aforementioned kit automatically. As a result, not only the procedure has simplified and accelerated, but also became possible to obtain a certain level of RNA, independent from the skills of operators.

Examples of an automated apparatus which automatically proceeds the steps of separating and purifying RNA from a test sample containing nucleic acid by using a cartridge for separation and purification of nucleic acid receiving the nucleic acid-adsorbing porous membrane in a container having at least two openings and a pressure difference-generating apparatus, but the automated apparatus of the invention is not limited thereto.

An automated apparatus for selectively separating and purifying RNA automatically performing the operations for separation and purification, the operations comprising the steps of: using a cartridge for separation and purification of nucleic acid receiving a nucleic acid-adsorbing porous membrane which solutions can internally pass through; injecting a nucleic acid mixture solution containing DNA and RNA into the cartridge for separation and purification of nucleic acid, so as to adsorb nucleic acid in the nucleic acid mixture solution onto the nucleic acid-adsorbing porous membrane by pressurizing; afterwards, injecting a washing solution into the cartridge for separation and purification of nucleic acid, so as to remove the impurities by pressurizing; injecting a DNase into the cartridge for separation and purification of nucleic acid, so as to subject the nucleic acid-adsorbing porous membrane to DNase treatment, and passing DNase through the internal nucleic acid-adsorbing porous membrane by pressurizing; afterwards, injecting a washing solution into the cartridge for separation and purification of nucleic acid, so as to remove the degradation product of DNA by pressurizing; afterwards, injecting a recovering solution into the cartridge for separation and purification of nucleic acid, so as to desorb the adsorbed RNA from the nucleic acid-adsorbing porous membrane, and recovering the desorbed RNA along with recovering solution, wherein the automated apparatus which comprises: a loading mechanism which maintains: the cartridge for separation and purification of nucleic acid; a waste solution container receiving the nucleic acid mixture solution residue and the eluted solution of DNase and the washing solution; and a recovering container receiving the recovering solution containing recovered RNA, a pressurized air supplying mechanism which introduce a pressurized air into the cartridge for separation and purification of nucleic acid; and an injecting mechanism which injects a washing solution, DNase and a recovering solution into the cartridge for separation and purification of nucleic acid is preferred.

The loading mechanism is preferred to comprise: a stand loaded onto the main apparatus; a cartridge holder, which maintains the cartridge for separation and purification of nucleic acid, supported by the stand with being capable of moving up and down; and a container holder which maintains the waste solution container and the recovering container with being enable to exchange their positions against the cartridge for separation and purification of nucleic acid under the cartridge holder.

The pressurized air supplying mechanism is preferred to comprise: an air nozzle which spouts pressurized air from the bottom portion; a pressurized-head which moves the air nozzle up and down depending on the cartridge for separation and purification of nucleic acid maintained to the cartridge holder by supporting the air nozzle; and a position determining means installed in the pressurized-head which determines the position of the cartridge for separation and purification of nucleic acid in the rack of the loading mechanism.

Further, the injecting mechanism is preferred to comprise: a washing solution injecting nozzle which injects the washing solution; a DNase injecting nozzle which injects DNase; a recovering solution injecting nozzle which injects the recovering solution; a nozzle transfer board which can move subsequently on the cartridge for separation and purification of nucleic acid maintained to the loading mechanism with maintaining the washing solution injecting nozzle, the DNase injecting nozzle and the recovering solution injecting nozzle; a washing solution supplying pump which supplies the washing solution to the washing solution injecting nozzle by sucking the washing solution from a washing solution bottle receiving the washing-solution; a DNase supplying pump which supplies DNase to the DNase injecting nozzle by sucking DNase from a DNase bottle receiving DNase; and a recovering solution supplying pump which supplies the recovering solution to the recovering solution injecting nozzle by sucking the recovering solution from a recovering solution bottle receiving the recovering solution.

According to an automated apparatus, for example aforementioned automated apparatus comprising: the cartridge for separation and purification of nucleic acid; the loading mechanism which maintains the waste solution container and the recovering container, the pressurized air supplying mechanism which introduce a pressurized air into the cartridge for separation and purification of nucleic acid; and the injecting mechanism which injects a washing solution, DNase and a recovering solution into the cartridge for separation and purification of nucleic acid, the mechanism which automatically proceeds the following steps for separating and purifying RNA: injecting a nucleic acid mixture solution containing nucleic acid into the cartridge for separation and purification of nucleic acid receiving the nucleic acid-adsorbing porous membrane, so as to adsorb nucleic acid onto the nucleic acid-adsorbing porous membrane by pressurizing; injecting a washing solution, so as to remove the impurities; injecting a DNase into the cartridge for separation and purification of nucleic acid, so as to provide DNase action in the nucleic acid-adsorbing porous membrane, and passing DNase through the internal nucleic acid-adsorbing porous membrane by pressurizing; injecting a washing solution into, so as to remove the degradation product of DNA by pressurizing, injecting a recovering solution, so as to desorb the adsorbed RNA from the nucleic acid-adsorbing porous membrane, and recovering the desorbed RNA, and the mechanism which can automatically separate and purify RNA in a mixture solution containing nucleic acid in a short time with high efficiency, can be compactly constituted.

Further, when the loading mechanism comprises: a stand; a cartridge holder, which enables up and down movement, maintaining the cartridge for separation and purification of nucleic acid; and a container holder which maintains the waste solution container and the recovering container with being enable to exchange their positions, a cartridge for separation and purification of nucleic acid and both container set, and the waste solution container and the recovering container can be easily exchanged.

Further, when the pressurized air supplying mechanism comprises: an air nozzle; a pressurized-head head which moves the air nozzle up and down; a position determining means which determines position of the cartridge for separation and purification of nucleic acid, a reliable supply of a pressurized air can be performed with a simple mechanism.

Further, when the injecting mechanism comprises: a washing solution injecting nozzle; a DNase injecting nozzle; a recovering solution injecting nozzle; a nozzle transfer board which can move subsequently on the cartridge for separation and purification of nucleic acid; a washing solution supplying pump which supplies the washing solution to the washing solution injecting nozzle by sucking the washing solution from a washing solution bottle; and the recovering solution supplying pump which supplies the recovering solution to the recovering solution injecting nozzle by sucking the recovering solution from a recovering solution bottle, the sequential injections of the washing solution and the recovering solution can be performed with a simple mechanism.

(2-c) Step of Desorbing RNA from the Nucleic Acid-Adsorbing Porous Membrane by Using the Recovering Solution, and Recovering RNA (2-c) The step of recovering RNA by desorbing it from the nucleic acid-adsorbing porous membrane is shown as follows.

In the recovery step, the recovering solution is provided to the cartridge for separation and purification of nucleic acid, which receives the nucleic acid-adsorbing porous membrane, using a tube, a pipette, an automatic injection unit, or a supply means having similar functions. The recovering solution can be provided from one opening of the cartridge for separation and purification of nucleic acid (the one opening where a sample solution containing nucleic acid is injected), and a pressure difference-generating apparatus (for example, a dropper, a syringe, a pump, a power pipette, etc.) connected to the opening is used, thereby making an inside of the cartridge for separation and purification of nucleic acid into a pressurized state, so as to pass the recovering solution through the nucleic acid-adsorbing porous membrane, and discharge the recovering solution from another opening different from the one opening. Additionally, the recovering solution can be provided into one opening and discharged from the same opening. Further, the recovering solution can be provided to another opening different from the one opening which the nucleic acid mixture solution containing nucleic acid is provided to, and discharged from the same opening. Among them, providing into one opening of the cartridge for separation and purification of nucleic acid, passing through nucleic acid-adsorbing porous membrane and discharging from another opening different from the one opening is much preferred due to its excellent recovering efficiency.

Considering the volume of the sample solution containing nucleic acid, which was prepared from the test sample, the desorption of the nucleic acid can be conducted by controlling the volume of the recovering solution. The amount of the recovering solution containing separated and purified nucleic acid is related to the amount of a test sample used at the time. In general, the amount of the recovering solution commonly used is from several 10 µl to several 100 µl, but either an extremely small quantity of a test sample is used or on the other hand a large amount of a nucleic acid is desired to be separated and purified, the amount of the recovering solution can be changed in a range of 1 µl to several 10 ml.

For the recovering solution, purified distilled water, Tris/EDTA buffer and the like can preferably be used. Further, when providing the recovered nucleic acid to a PCR (Polymerase Chain Reaction), the buffer solution (for example, an aqueous solution having the final concentration of 50 mmol/L of KCl, 10 mmol/L of Tris-HCl, and 1.5 mmol/L of $MgCl_2$) for the PCR can be used.

The pH of the recovering solution is preferably from pH 2 to 11, more preferably from pH 5 to 9. Further, the recovering solution having ion strength of 500 mmol/L or less is preferred, and having a salt concentration of 50 to 0.01 mmol/L of is more preferred. Especially, the ion strength and the salt concentration have effects on the elution of the adsorbed nucleic acid. The recovering solution having the ion strength of 290 mmol/L or less and the salt concentration of 90 mmol/L or less is preferred. Thereby, the recovering percentage of nucleic acid increases, and thus a larger amount of nucleic acid can be recovered.

A recovering solution containing concentrated nucleic acid can be obtained by reducing volume of the recovering solution in comparison with the volume of the original sample solution containing nucleic acid. Preferably, (volume of recovering solution):(volume of sample solution)=from 1:100 to 99:100, and more preferably, (volume of recovering solution):(volume of sample solution)=from 1:10 to 9:10. By this, nucleic acid can be conveniently concentration without carrying out an operation for concentration at the after-step of the nucleic acid separation purification. By these methods, a method for obtaining nucleic acid solution in which nucleic acid is concentrated than the test sample can be provided.

In addition, as another method, a recovering solution containing a desired concentration of nucleic acid can be obtained, and a recovering solution containing a concentration of nucleic acid suited for the next step (PCR or the like) can be obtained, by carrying out desorption of nucleic acid under such a condition that volume of the recovering solution becomes larger than the volume of the original sample solution containing nucleic acid. Preferably, (volume of recovering solution):(volume of sample solution)=from 1:1 to 50:1, and more preferably, (volume of recovering solution):(volume of sample solution)=from 1:1 to 5:1. By this, a merit, namely avoidance of the troublesome concentration adjustment after the separation and purification of nucleic acid, can be obtained. In addition, increase of nucleic acid recovery ratio from the porous membrane can be made by the use of sufficient amount of the recovering solution.

Also, nucleic acid can be conveniently recovered by changing temperature of the recovering solution in response to the purpose. For example, nucleic acid solution can be obtained conveniently and efficiently, by preventing degradation of nucleic acid through the inhibition of the action of nuclease without adding a certain reagent or a special operation capable of inhibiting enzymatic degradation, by carrying out desorption of nucleic acid from the porous membrane after changing temperature of the recovering solution from 0 to 10° C.

Also, when temperature of the recovering solution is set to 10 to 35° C., recovery of nucleic acid at general room temperature can be carried out and the nucleic acid can be separated and purified by desorbing it without requiring a complex step.

In addition, as another method, desorption of nucleic acid from the porous membrane can be carried out conveniently with high recovery ratio without mediating a complicated operation, by shifting temperature of the recovering solution to a high temperature of, for example, from 35 to 70° C.

The number of times of injection of the recovering solution is not limited, and it may be once or two or more times. In general, this is carried out by single recovery when nucleic acid is separated and purified quickly and conveniently, but when a large amount of nucleic acid is recovered, the recovering solution is injected two or more times in some cases.

In the recovery step, it is possible to make the recovering solution of nucleic acid into a composition which can be used in the after-step thereafter. The separated and purified nucleic acid is sometimes amplified by the PCR (polymerase chain reaction) method. In that case, the separated and purified nucleic acid solution must be diluted with a buffer solution suited for the PCR method. By using a buffer solution suited for the PCR method in the recovery step by this method, it can be shifted to the subsequent PCR step conveniently and quickly.

Also, in the recovery step, it is possible to add a stabilizing agent for preventing degradation of nucleic acid recovered in the recovering solution of nucleic acid. As the stabilizing agent, an antibacterial agent, a fungicide, a nuclease inhibitor and the like can be added. As the nuclease inhibitor, EDTA and the like can be cited. In addition, as another embodiment, a stabilizer can also be added to the recovery container in advance.

Also, the recovery container to be used in the recovery step is not particularly limited, a recovery container prepared from a raw material having no absorption at 260 nm can be used. In that case, concentration of the recovered nucleic acid solution can be measured without transferring it into other container. As the raw material having no absorption at 260 nm, for example quartz glass and the like can be used, though not limited thereto.

As disclosed above, for the method for separating and purifying nucleic acid from a test sample containing nucleic acid by using a cartridge for separation and purification of nucleic acid receiving the nucleic acid-adsorbing porous membrane in a container having at least two openings and a pressure difference-generating apparatus, wherein the method is conducted preferably by using an automated apparatus which proceeds the steps automatically comprised in the method. As a result, not only the procedure is simplified and accelerated, but also became possible to obtain a certain level of nucleic acid, independent from the skills of operators.

Examples of an automated apparatus which automatically proceeds the steps of separating and purifying nucleic acid from a test sample containing nucleic acid by using a cartridge for separation and purification of nucleic acid receiving the nucleic acid-adsorbing porous membrane in a container having at least two openings and a pressure difference-generating apparatus, but the automated apparatus of the invention is not limited thereto.

An automated apparatus for selectively separating and purifying nucleic acid automatically performing the operations for separation and purification, the operations comprising the steps of: using a cartridge for separation and purification of nucleic acid receiving a nucleic acid-adsorbing porous membrane which solutions can internally pass through; injecting a nucleic acid mixture solution containing nucleic into the cartridge for separation and purification of nucleic acid, so as to adsorb nucleic acid in the nucleic acid mixture solution onto the nucleic acid-adsorbing porous membrane by pressurizing; afterwards, injecting a washing solution into the cartridge for separation and purification of nucleic acid, so as to remove the impurities by pressurizing; injecting a recovering solution into the cartridge for separation and purification of nucleic acid, so as to desorb the adsorbed nucleic acid from the nucleic acid-adsorbing porous membrane along with the recovering solution, wherein the automated apparatus is characterized in comprising: a loading mechanism which maintains: the cartridge for separation and purification of nucleic acid; a waste solution container receiving the eluted solution of the sample solution and the washing solution; and a recovering container receiving the recovering solution containing recovered nucleic acid, a pressurized air supplying mechanism which introduce a pressurized air into the cartridge for separation and purification of nucleic acid; and an injecting mechanism which injects a washing solution and a recovering solution into the cartridge for separation and purification of nucleic acid.

EXAMPLES

The present invention is described in detail according to Examples below, but the invention is not limited the following Examples.

Example 1

(1-1) Preparation of Cartridge for Separation and Purification of Nucleic Acid

The cartridge for separation and purification of nucleic acid, which has a portion for receiving the nucleic acid-adsorbing porous membrane having an inner diameter of 7 mm was made.

(1-2) For the Nucleic Acid-Adsorbing Porous Membrane, a Porous Membrane which is the Saponified Porous Membrane of Triacetyl Cellulose was Used, and the Nucleic Acid-Adsorbing Porous Membrane was Received in the Nucleic Acid-Adsorbing Porous Membrane Accommodation Portion of the Cartridge for Separation and Purification of Nucleic Acid Prepared in the Above (1-1).

Example 1-1

(1-3) Preparation of Nucleic Acid-Solubilizing Reagent, Washing Solution and Recovering Solution A nucleic acid-solubilizing reagent A-1, a washing solution A-1 and a recovering solution A-1 were prepared according to the formulation indicated below.

| (Nucleic acid-solubilizing reagent A-1) | |
|---|---|
| Guanidine hydrochloride (manufactured by Life Technology Inc.) | 382 g |
| Tris (manufactured by Life Technology Inc.) | 12.1 g |
| TritonX-100 (manufactured by ICN Biochemicals Inc.) | 10 g |
| Distilled water | Add up to 1000 ml |
| 1.0 vol % of 2-mercaptoethanol is added right before the use of nucleic acid-solubilizing reagent A-1. | |
| (Washing solution A-1) | |
| 10 mmol/L Tris-HCL (pH7.5) | 30% by volume ethanol |
| (Recovering solution A-1) | |
| 1 mmol/L Tris-HCl (pH 6.5) | |

(1-4) Preparation of Mixture Solution of Nucleic Acid

A culture solution (RPMI1640-10% fetal calves serum) of human acute promyelocytic leukemia cell (HL60) was incubated under existent of 5% $CO_2$ at 37° C. The cells were prepare to contain $1\times10^6$ cells, and were washed in the $Ca^{2+}$, $Mg^{2+}$ free-PBS. 300 g of prepared cells were centrifuged with a swing rotor at 4° C. for 5 minutes, and the floating cells were palletized, and the supernatant was removed, and the cell were suspended by tapping. 350 µl of nucleic acid-solubilizing reagent A-1 was added thereto, and was stirred using a Vortex mixer for 1 minute. Next, 350 µl of 70 vol % ethanol was added thereto, and was stirred using the Vortex mixer for 5 seconds, thereby the mixture solution of nucleic acid for Example 1-1 was obtained.

(1-5) Procedures for Separating and Purifying RNA

The mixture solution of nucleic acid obtained from the above (1-4) was injected into one opening of the cartridge for separation and purification of nucleic acid receiving the nucleic acid-adsorbing porous membrane prepared in (1-1) and (1-2) above, afterwards a pressure difference-generating apparatus (syringe pump) was connected to the one opening to make an inside of the cartridge for separation and purification of nucleic acid into a pressurized state (260 kPa), so as to contact the injected mixture solution of nucleic acid with the nucleic acid-adsorbing porous membrane by passing the injected mixture solution of nucleic acid through the nucleic acid-adsorbing porous membrane and discharge them from another opening. Further, after taking off the pressure difference-generating apparatus, 500 µl of the washing solution A-1 was injected into the one opening of the cartridge for separation and purification of nucleic acid, afterwards a pressure difference-generating apparatus (syringe pump) was connected to the one opening to make the inside of the cartridge for separation and purification of nucleic acid into a pressurized state (260 kPa), so as to pass the injected washing solution A-1 through the nucleic acid-adsorbing porous membrane and discharge them from another opening (washing step 1). After taking off the pressure difference-generating apparatus, 10 µl (26 µl/cm²) of DNase solution (RNase-Free DNase Set 341 Kunitz U/mL, manufactured by Qiagen Inc. was used. DNase solution was prepared in accordance with the attached protocols.) was applied onto the membrane, and was set for 15 minutes. The washing procedure was repeated twice in the same way (washing step 2). Further, after taking off the pressure difference-generating apparatus, 100 µl of the recovering solution A-1 was injected into the one opening of the cartridge for separation and purification of nucleic acid, and a pressure difference-generating apparatus (syringe pump) was connected to the one opening of the cartridge for separation and purification of nucleic acid to make the inside of the cartridge for separation and purification of nucleic acid into a pressurized state (260 kPa), so as to pass the injected recovering solution A-1 through the nucleic acid-adsorbing porous membrane and discharge them from another opening, thereby the eluted solution was recovered.

In addition, the procedure for separating and purifying RNA was conducted in the same manner except the amount of the DNase solution was changed 10 µl to 20 µl, 40 µl. Further, as a reference example, the procedure for separating and purifying RNA was conducted in the same manner except the amount of the DNase solution was changed 10 µl to 80 µl.

Comparative Example 1-1

RNA was extracted in the same procedure as Example 1-1, except that the DNase solution was not applied. In this case, for the washing step, only the washing step 1 was repeated 3 times in the same way, which was different from Example 1-1 wherein the total repetition of the washing steps 1 and 2 was 3 times.

Comparative Example 1-2

RNA extraction was conducted according to the same protocol of the kit using RNeasy Mini Kit manufactured by Qiagen Inc. from the cultured cells ($1\times10^6$ cells) in the same procedure as Example 1-1. The amount of DNase solution was used according to the protocol of 3 methods of 80 µl (208 µl/cm²), and the reduced amount of 20 µl (52 µl/cm²) and 10 µl (26 µl/cm²).

Comparative Example 1-3

RNA was extracted in the same procedure as Comparative Example 1-2, except that DNase solution was not applied. At this time, the procedure was conducted according to the RNeasy Mini Kit protocol which did not conduct the DNase treatment.

(1-6) Agarose Gel Electrophoresis of Recovered Nucleic Acid

Figure 2:
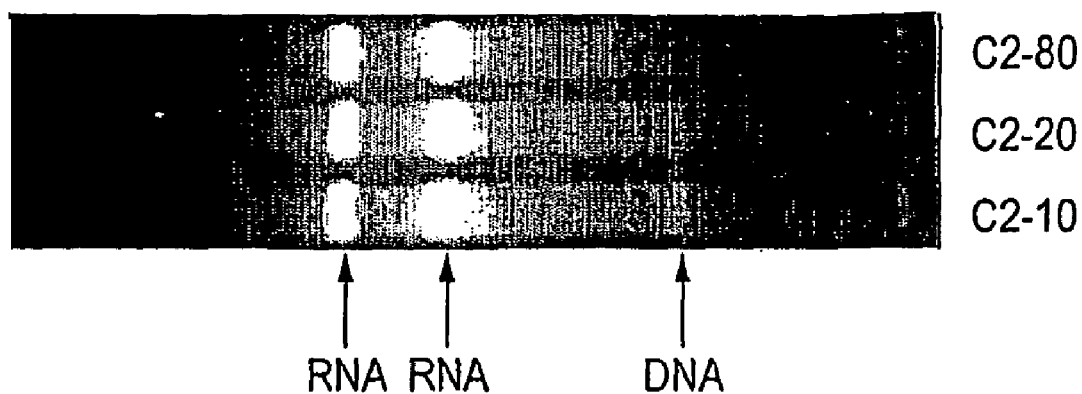
FIG. 2 is a view of a photo obtained by conducting electrophoresis using 1% agarose gel of the recovering solution containing recovered nucleic acid in accordance with Comparative Example 1-2.
Figure 3:
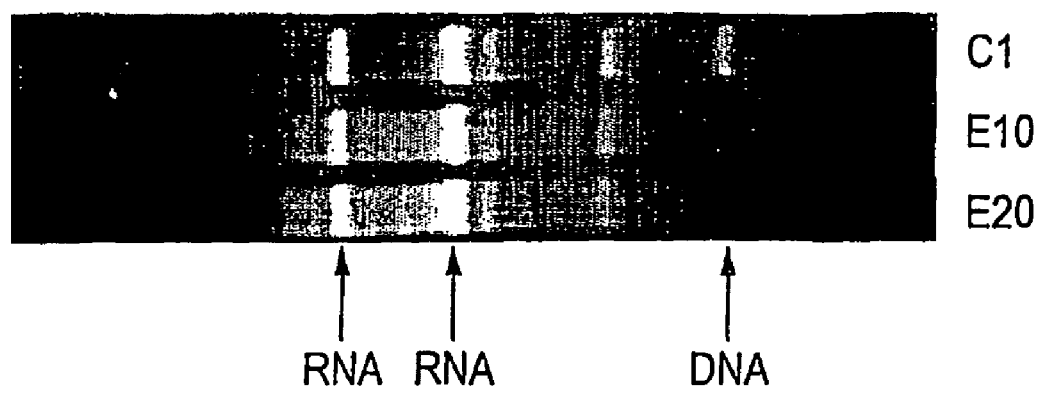
FIG. 3 is a view of a photo obtained by conducting electrophoresis using 1% agarose gel of the recovering solution containing recovered nucleic acid in accordance with Example 1-1 and Comparative Example 1-1.

FIGS. 1 to 3 shows the results of electrophoresis using 1% agarose gel of the recovering solution containing the recovered nucleic acid in accordance with Example 1-1 and Comparative Example 1-1, 1-2 and 1-3

In Comparative Example 1-2, 80 µl (208 µl/cm²) of the DNase solution is required, but in Example 1-1, DNA degradation is possible even though the using amount of the DNase solution was less than in Comparative Example 1-2. And the DNA derived band detected in Comparative 1-1 was not detected in Example 1-1. Surprisingly, the invention was able to degrade DNA in case of using only 10 µl (26 µl/cm²) of the DNase solution.

From the result, it was found in the invention that RNA could be selectively recovered by degrading DNA in a mixture solution of nucleic acid containing DNA and RNA even though the using amount of DNase solution was small.

Example 1-2

Using HeLa cell as an adhesive cell, a mixture solution of nucleic acid can be obtained by On-dish method as follows.

On a plate for cultured cells, HeLa cell was incubated in a culture solution (MEM-10% fetal calves serum) under existence of 5% $CO_2$ at 37° C. After removing the culture solution from the plate for the cultured cells, 350 µl of the nucleic acid-solubilizing reagent A-1 per $1.5 \times 10^6$ HeLa cells were added to obtain a cell dissolved solution. This solution was stirred by pipetting, and was recovered to another container.

To the recovering solution, 350 µl of 70 vol % ethanol was added, and was stirred using Vortex mixer to obtain a mixture solution of nucleic acid. The obtained mixture solution of nucleic acid was conducted a procedure for separating and purifying RNA in the same procedure as (1-5) in Example 1-1. In addition, the amount of DNase solution used in a procedure for separating and purifying RNA was 10 µl.

Example 1-3

Using HeLa cell as an adhesive cell, a mixture solution of nucleic acid was obtained after trypsinization as follows.

On a container for incubating adhesive cells, HeLa cell was incubated in a culture solution (MEM-10% fetal calves serum) under existence of 5% $CO_2$ at 37° C. After removing the culture solution from the container, 0.25% of trypsin was added and treated so that the adhesive cells are exfoliated from the adhesive cell incubating container, and the number of cells were counted for. The mixture was centrifuged 1000 rotation for 3 minutes using a centrifuge for cells, thereby removing the supernatant to collect HeLa cells. To the cell precipitate after centrifuge, 350 µl of the nucleic acid-solubilizing reagent A-1 per $5 \times 10^5$ cells were added. This solution was stirred vigorously using a Vortex mixer for 1 minute to dissolve cells. To the solution, 350 µl of 70 vol % ethanol was added, and was stirred using the Vortex mixer for 5 seconds to obtain a mixture solution of nucleic acid. The obtained mixture solution of nucleic acid was conducted a procedure for separating and purifying RNA in the same procedure as (1-5) in Example 1-1. In addition, the amount of the DNase solution used in a procedure for separating and purifying RNA was 10 µl.

Comparative Example 1-4

Procedures for separating and purifying RNA were conducted according to the same protocol of the kit using commercially available RNeasy Mini Kit (manufactured by Qiagen Inc.) from the mixture solution of nucleic acid of Example 1-2. In addition, 80 µl of DNase solution was used in the procedure for separating and purifying RNA.

Comparative Example 1-5

Procedures for separating and purifying RNA using the mixture solution of nucleic acid of Example 1-3 were conducted in the same procedure as Comparative Example 1-4.

The amount of the RNA recovered in the recovering solution containing the recovered nucleic acid from Example 1-2 and Example 1-3, and Example 1-4 and Example 1-5 was measured. The measurement was conducted using absorbance at the wavelength of 260 nm. The results are shown in Table 1-1.

TABLE 1-1

| | Example | | Comparative Example | |
|---|---|---|---|---|
| | No. | Amount of Recovered RNA (µg) | No. | Amount of Recovered RNA (µg) |
| On-dish Method ($1.5 \times 10^6$) | Example 1-2 | 28.9 | Comparative Example 1-4 | 24.2 |
| Trypsinization Method ($5 \times 10^5$) | Example 1-3 | 13.5 | Comparative Example 1-5 | 11.9 |

Next, the recovering solution containing recovered nucleic acid from Example 1-3 and Comparative Example 1-5 were electrophoresed using MOPS-formamide electrophoresis. The results are shown in FIG. 4.

Figure 4:
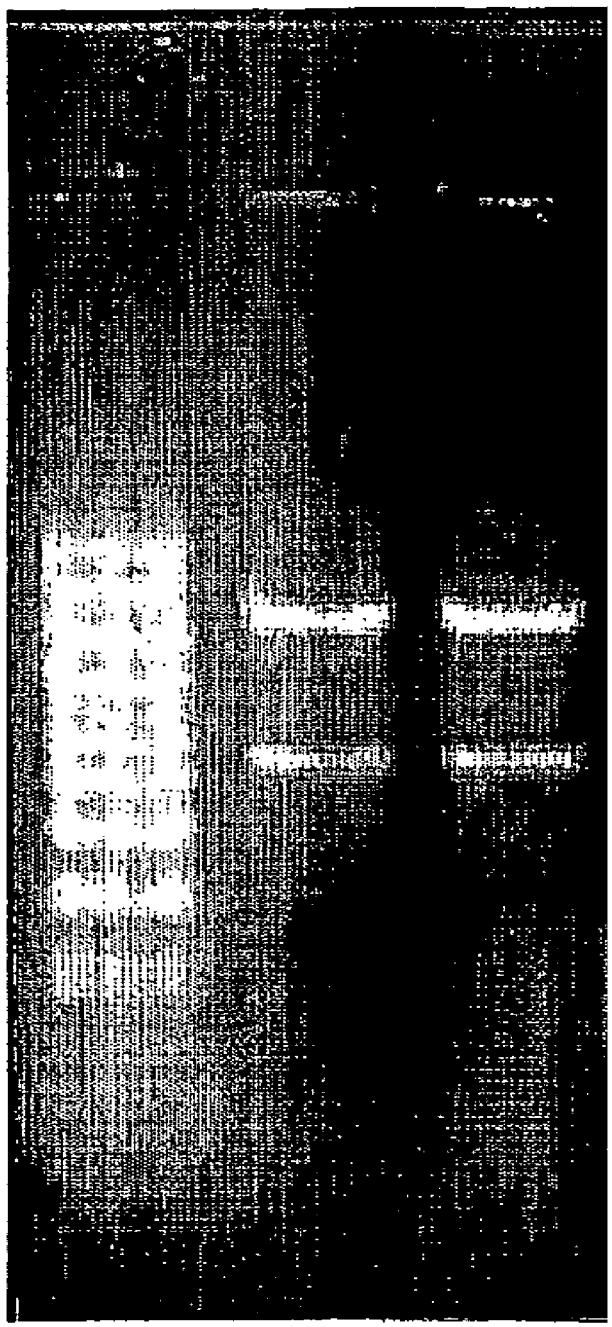
FIG. 4 is a view of a photo obtained by conducting electrophoresis by MOPS-formamide electrophoresis method of the recovering solution containing recovered nucleic acid in accordance with Example 1-3 and Comparative Example 1-5.

In FIG. 4, Band 1 obtained from electrophoresing the recovered nucleic acid in Example 1-3 had high quality RNA having equal purity and not having degrading RNA compared to Band 2 of Comparative Example 1-5 using a commercially available purifying kit.

Further, as shown from Table 1-2, it was found that this Example using a method for selectively separating and purifying RNA of the invention, the obtained RNA has an equivalent quality and a large recovered amount, compared to Comparative Example using a commercially available kit.

Example 1-4

(1-7) Preparation of Nucleic Acid-Solubilizing Reagent B-1 (B-1-1 and B-1-2), Washing Solution B-1, and Recovering Solution B-1

A nucleic acid-solubilizing reagent, a washing solution, and a recovering solution were prepared according to the formulation indicated below

| (Nucleic Acid-Solubilizing Reagent B-1-1) | |
|---|---|
| Guanidine thiocyanate (manufactured by Wako Pure Chemical Industries, Ltd.) | 3.5 mol/L |
| BisTris (manufactured by Dojindo Laboratories) | 0.25 mol/L |
| Hydrochloric acid is used to prepare the solution in pH 6.5 | |
| 1.0 vol % of 2-mercaptoethanol is added right before the use of nucleic acid-solubilizing reagent B-1-1. | |

| (Nucleic Acid-Solubilizing Reagent B-1-2) | |
|---|---|
| Tween20 (manufactured by Wako Pure Chemical Industries, Ltd.) | 15% by weight |
| BisTris (manufactured by Dojindo Laboratories) | 0.1 mol/L |
| Hydrochloric acid is used to prepare the solution in pH 6.0 | |

| (Washing solution B-1) | |
|---|---|
| Tris-HCl (pH 7.5) | 10 mmol/L |
| Sodium chloride | 0.5 mol/L |
| Ethanol | 10% by volume |

| (Recovering solution B-1) | |
|---|---|
| Tris-HCl (pH 6.5) | 1 mmol/L |

(1-8) Preparation of Mixture Solution of Nucleic Acid

A mouse liver quickly frozen under liquid nitrogen was cut into small pieces, and 5 mg thereof was incubated in a 1.5 ml tube. 350 µl of the nucleic acid-solubilizing reagent B-1-1 was added thereto, and was put into a Rotor-Stator Homogenizer (Polytron, manufactured by KINEMATICA Inc.) until the mixture became homogeneous. The solution was than centrifuged at 8000×g for 3 minutes at room temperature, and to a new 1.5 ml tube, the supernatant was transferred trying not to take the tissue fragments. 175 μl of the nucleic acid-solubilizing reagent B-1-2 was added thereto, and was stirred using a Vortex mixer for 15 seconds. Further, 175 μl of 99.5 vol % or more superhigh grade ethanol was added thereto, and was stirred using Vortex mixer for 1 minute.

(1-9) Procedures for Separating and Purifying RNA

The mixture solution of nucleic acid obtained from the above (1-9) was injected into the cartridge for separation and purification of nucleic acid comprising the nucleic acid-adsorbing porous membrane as described in the above (1-1) and (1-2), afterwards a pressure difference-generating apparatus (syringe pump) was connected to the one opening to make an inside of the cartridge for separation and purification of nucleic acid into a pressurized state (260 kPa), so as to contact the injected mixture solution of nucleic acid with the nucleic acid-adsorbing porous membrane by passing the injected mixture solution of nucleic acid through the nucleic acid-adsorbing porous membrane and discharge them from another opening. Further, after taking off the pressure difference-generating apparatus, 500 μl of the washing solution B-1 was injected into the one opening of the cartridge for separation and purification of nucleic acid, afterwards a pressure difference-generating apparatus (syringe pump) was connected to the one opening to make the inside of the cartridge for separation and purification of nucleic acid into a pressurized state (120 kPa), so as to pass the injected washing solution B-1 through the nucleic acid-adsorbing porous membrane and discharge them from another opening (washing step 1). After taking off the pressure difference-generating apparatus, 10 μl (26 μl/cm$^2$) of DNase solution (RQ1 RNase-Free DNase 500 Kunitz U/mL, manufactured by Promega Corp. was used. This reaction solution contains 40 mM Tris-HCl(pH8.0), 5 mM HEPES, 10 mM MgSO$_4$, 5 mM MgCl$_2$, 6 mM CaCl$_2$ and 25% Glycerol.) was applied onto the membrane, and was set for 5 minutes. The washing procedure was repeated twice in the same way (washing step 2). Further, after taking off the pressure difference-generating apparatus, 100 μl of the recovering solution B-1 was injected into the one opening of the cartridge for separation and purification of nucleic acid, and a pressure difference-generating apparatus (syringe pump) was connected to the one opening of the cartridge for separation and purification of nucleic acid to make the inside of the cartridge for separation and purification of nucleic acid into a pressurized state (120 kPa), so as to pass the injected recovering solution B-1 through the nucleic acid-adsorbing porous membrane and discharge them from another opening, thereby the eluted solution was recovered.

Comparative Example 1-6

RNA extraction was conducted according to the same protocol of the kit using RNeasy Mini Kit manufactured by Qiagen Inc. using the mouse liver as in the procedure (1-8). The amount of DNase solution was used according to the protocol of 80 μl (208 μl/cm$^2$).

The amount of the recovered RNA in the recovering solution containing recovered nucleic acid from Example 1-4 and Comparative Example 1-6 was measured. The measurement was conducted using absorbance at the wavelength of 260 nm. The results are shown in Table 1-2.

TABLE 1-2

|  | Amount of Recovered RNA (μg) |
| --- | --- |
| Example 1-4 | 21.6 |
| Comparative Example 1-6 | 18.8 |

The recovering solution containing nucleic acid recovered from Example 1-4 and Comparative Example 1-6 were electrophoresed using 1% agarose electrophoresis. The results are shown in FIG. 5.

Figure 5:
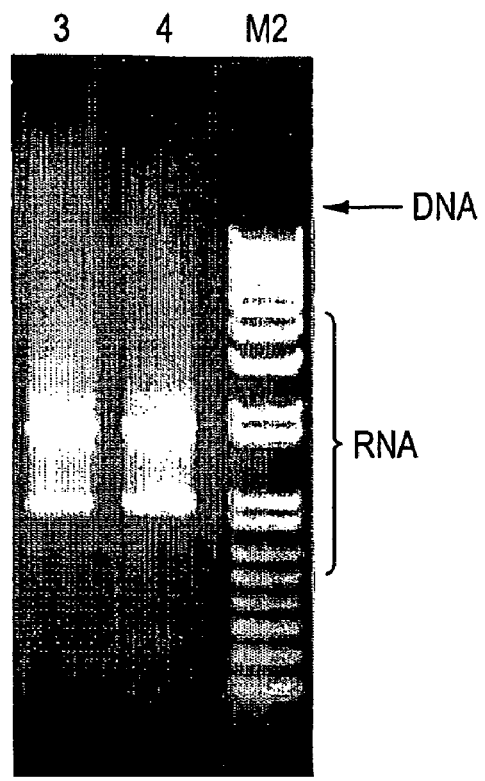
FIG. 5 is a view of a photo obtained by conducting electrophoresis using 1% agarose gel of the recovering solution containing recovered nucleic acid in accordance with Example 1-4 and Comparative Example 1-6.

In the electrophoresis results of FIG. 5, Band 4 in Comparative Example 1-6 required 80 μl (208 μl/cm$^2$) of DNase solution, but Band 3 in Example 1-4 DNA degraded by using only 10 μl (26 μl/cm$^2$) of DNase solution. Example 1-4 had high quality RNA having equal purity and not having degrading of RNA compared to Comparative Example 1-6.

In addition, according to Table 1-2, Example using the method for selectively separating and purifying RNA of the present invention obtained RNA having same quality and larger amount of recovered thereof compared to the Comparative Example using commercially available purifying kit.

From the above, it was found that even in the case of an animal tissue as a test sample, using small amount of DNase solution could degrade DNA in the mixture solution of nucleic acid containing DNA and RNA, thereby selectively recovering RNA.

Example 1-5

(1-10) Preparation of a Mixture Solution of Nucleic Acid

A mouse spleen quickly frozen under liquid nitrogen was cut into small pieces, and 10 mg thereof was incubated in a 2 ml of Safe Lock Tube (manufactured by Eppendorf, Inc.). 350 μl of a nucleic acid-solubilizing reagent B-1-1 and a zirconia ball having diameter of 5 mm were added thereto. The solution was homogenized using TissueLyzer (manufactured by Qiagen Inc.) set at 20 Hz for 3 minutes twice. The solution was than centrifuged at 8000×g for 3 minutes at room temperature, and to a new 1.5 ml tube, the supernatant was transferred trying not to take the tissue fragments. 175 μl of the nucleic acid-solubilizing reagent B-1-2 was added thereto, and was stirred using a Vortex mixer for 15 seconds. Further, 175 μl of 99.5 vol % or more superhigh grade ethanol was added thereto, and was stirred using Vortex mixer for 1 minute.

(1-11) Procedures for Separating and Purifying RNA

RNA was recovered in the same procedure as (1-9). In the same manner, 10 μl (26 μl/cm$^2$) of DNase solution (RQ1 RNase-Free DNase 500 Kunitz U/mL, manufactured by Promega Corp. was used) was applied onto the membrane.

Comparative Example 1-7

RNA extraction was conducted according to the same protocol of the kit using RNeasy Mini Kit manufactured by Qiagen Inc. with a homogenized manner using the spleen of a mouse as in the procedure (1-10). The amount of DNase solution was used according to the protocol of 80 μl (208 μl/cm$^2$).

The recovering solution containing recovered nucleic acid from Example 1-5 and Comparative Example 1-7 were electrophoresed using 1% agarose electrophoresis. The results are shown in FIG. 6.

Figure 6:
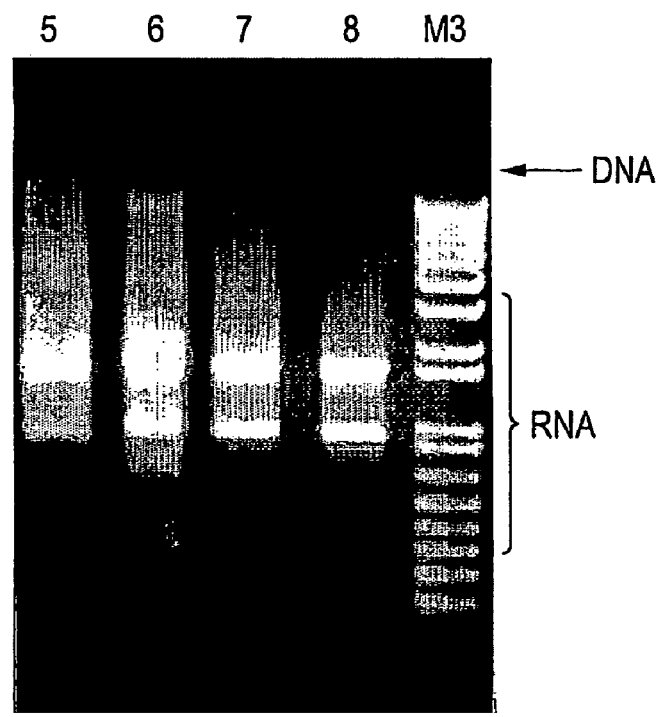
FIG. 6 is a view of a photo obtained by conducting electrophoresis using 1% agarose gel of the recovering solution containing recovered nucleic acid in accordance with Example 1-5 and Comparative Example 1-7, and Example 1-6 and Comparative Example 1-8.

In the electrophoresis result of FIG. 6, Band 6 in Comparative Example 1-7 using 80 μl (208 μl/cm$^2$) of DNase solution still was feeble but recognized as a genome DNA band, meanwhile Band 5 in Example 1-5 using only 10 μl (26 μl/cm$^2$) of DNase solution degraded DNA. In Example 1-5 using small amount of DNase solution compared to Comparative Example 1-7, a more satisfactory purity of RNA was recovered.

Example 1-6

(1-12) Preparation of a Mixture Solution of Nucleic Acid

A mouse liver quickly frozen under liquid nitrogen was cut into small pieces, and 5 mg thereof was incubated in a 1.5 ml Tube, 350 μl d of the nucleic acid-solubilizing reagent B-1-1 was added thereto, and the solution was homogenized by attaching to PELLET PESTLES (manufactured by Kimble/Kontes Inc.) to its exclusive motor. The solution was than centrifuged at 8000×g for 3 minutes at room temperature, and to a new 1.5 ml tube, the supernatant was transferred trying not to take the tissue fragments. 175 μl of the nucleic acid-solubilizing reagent B-1-2 was added thereto, and was stirred using Vortex mixer for 15 seconds. Further, 175 μl of 99.5% or more superhigh grade ethanol was added thereto, and was stirred using Vortex mixer for 1 minute.

(1-13) Procedures for Separating and Purifying RNA

RNA was recovered in the same procedure as (1-9). In the same manner, 10 μl (26 μl/cm$^2$) of DNase solution (RQ1 RNase-Free DNase 500 Kunitz U/mL, manufactured by Promega Corp. was used) was applied onto the membrane.

Comparative Example 1-8

RNA extraction was conducted according to the same protocol of the kit using RNeasy Mini Kit manufactured by Qiagen Inc. with a homogenized manner using the mouse liver as in the procedure (1-12). The amount of DNase solution was used according to the protocol of 80 μl (208 μl/cm$^2$).

The recovering solution containing recovered nucleic acid from Example 1-6 and Comparative Example 1-8 were electrophoresed using 1% agarose electrophoresis. The results are shown in FIG. 6.

In the electrophoresis results of FIG. 6, Band 8 in Comparative Example 1-8 required 80 μl (208 μl/cm$^2$) of DNase solution, but Band 7 in Example 1-6, DNA degraded using only 10 μl (26 μl/cm$^2$) of DNase solution. Example 1-6 had high quality RNA having equal purity and not having degrading of RNA compared to Comparative Example 1-8.

Example 1-7

(1-14) Preparation of Nucleic Acid Mixture Solution

A mouse liver quickly frozen under liquid nitrogen was cut into small pieces, and 10 mg thereof was prepared in 2 ml of safe-rock tube (produced by Eppendorf Co., Ltd.). 350 μl of the nucleic acid-solubilizing reagent X shown in Table 1-3 was added thereto, further 5 mm diameter of zirconia ball was added. TissueLyzer (manufactured by Qiagen Inc.) was set to 20 Hz and homogenization was performed for 3 min at two times. The solution was then centrifuged at 10,000×g for 3 minutes at room temperature, and to a new 1.5 ml tube, the supernatant was transferred trying not to take the tissue fragments. The nucleic acid-solubilizing reagent Y as shown in Table 1-3 was added thereto, and was stirred using a Vortex mixer for 15 seconds. Further, superhigh grade ethanol having the concentrations as shown in Table 1-3 was added thereto, and was stirred using Vortex mixer for 1 minute.

TABLE 1-3

| Sample | Nucleic acid-solubilizing reagent X (containing 1.0vol % of 2-mercaptoethanol) | Nucleic acid-solubilizing reagent Y | Superhigh grade ethanol (vol %:μl) |
|---|---|---|---|
| A | RLT manufactured by Qiagen Inc. | None | 70 vol %:350 μl |
| B | RLT manufactured by Qiagen Inc. | None | 70 vol %:350 μl |
| C | RLT manufactured by Qiagen Inc. | None | 70 vol %:350 μl |
| D | RLT manufactured by Qiagen Inc. | None | 70 vol %:350 μl |
| E | RLT manufactured by Qiagen Inc. | nucleic acid-solubilizing reagent B-1-2:175 μl | 99.5 vol %:175 μl |
| F | RLT manufactured by Qiagen Inc. | nucleic acid-solubilizing reagent B-1-2:175 μl | 99.5 vol %:175 μl |
| G | RLT manufactured by Qiagen Inc. | nucleic acid-solubilizing reagent B-1-2:175 μl | 99.5 vol %:175 μl |
| H | RLT manufactured by Qiagen Inc. | nucleic acid-solubilizing reagent B-1-2:175 μl | 99.5 vol %:175 μl |
| I | nucleic acid-solubilizing reagent B-1-1 | None | 70 vol %:350 μl |
| J | nucleic acid-solubilizing reagent B-1-1 | None | 70 vol %:350 μl |
| K | nucleic acid-solubilizing reagent B-1-1 | None | 70 vol %:350 μl |
| L | nucleic acid-solubilizing reagent B-1-1 | None | 70 vol %:350 μl |
| M | nucleic acid-solubilizing reagent B-1-1 | nucleic acid-solubilizing reagent B-1-2:175 μl | 99.5 vol %:175 μl |
| N | nucleic acid-solubilizing reagent B-1-1 | nucleic acid-solubilizing reagent B-1-2:175 μl | 99.5 vol %:175 μl |
| O | nucleic acid-solubilizing reagent B-1-1 | nucleic acid-solubilizing reagent B-1-2:175 μl | 99.5 vol %:175 μl |
| P | nucleic acid-solubilizing reagent B-1-1 | nucleic acid-solubilizing reagent B-1-2:175 μl | 99.5 vol %:175 μl |

RLT manufactured by Qiagen Inc. represents the use of RNeasy Mini Kit RLT solution manufactured by Qiagen Inc..

(1-15) Procedures for Separating and Purifying RNA

The mixture solution of nucleic acid obtained from the above (1-14) was injected into the cartridge for separation and purification of nucleic acid comprising the nucleic acid-adsorbing porous membrane as described in the above (1-1) and (1-2), afterwards a pressure difference-generating apparatus (syringe pump) was connected to the one opening to make an inside of the cartridge for separation and purification of nucleic acid into a pressurized state (120 kPa), so as to contact the injected mixture solution of nucleic acid with the nucleic acid-adsorbing porous membrane by passing the injected mixture solution of nucleic acid through the nucleic acid-adsorbing porous membrane and discharge them from another opening. Further, after taking off the pressure difference-generating apparatus, 750 μl of the washing solution X as shown in Table 1-4 was injected into the one opening of the cartridge for separation and purification of nucleic acid, afterwards a pressure difference-generating apparatus (syringe pump) was connected to the one opening to make the inside of the cartridge for separation and purification of nucleic acid into a pressurized state (120 kPa), so as to pass the injected washing solution X through the nucleic acid-adsorbing porous membrane and discharge them from another opening (washing step 1). After taking off the pressure difference-generating apparatus, 40 μl (104 μl/cm$^2$) of DNase solution (RNase-Free DNase Set 341 Kunitz U/mL, manufactured by Qiagen Inc. was used. The washing procedure was repeated twice by using washing solution Y (washing step 2). Further, after taking off the pressure difference-generating apparatus, 100 μl of the recovering solution X as shown in Table 1-4 was injected into the one opening of the cartridge for separation and purification of nucleic acid, and a pressure difference-generating apparatus (syringe pump) was connected to the one opening of the cartridge for separation and purification of nucleic acid to make the inside of the cartridge for separation and purification of nucleic acid into a pressurized state (120 kPa), so as to pass the injected recovering solution X through the nucleic acid-adsorbing porous membrane and discharge them from another opening, thereby the eluted solution was recovered.

TABLE 1-4

| Sample | Washing solution X | Washing solution Y | Recovering solution X |
|--------|--------------------|--------------------|-----------------------|
| A | RW1 manufactured by Qiagen Inc. | RPE manufactured by Qiagen Inc. | RNase-Free water |
| B | RPE manufactured by Qiagen Inc. | RPE manufactured by Qiagen Inc. | RNase-Free water |
| C | RW1 manufactured by Qiagen Inc. | Washing solution B-1 | RNase-Free water |
| D | Washing solution B-1 | Washing solution B-1 | RNase-Free water |
| E | RW1 manufactured by Qiagen Inc. | RPE manufactured by Qiagen Inc. | RNase-Free water |
| F | RPE manufactured by Qiagen Inc. | RPE manufactured by Qiagen Inc. | RNase-Free water |
| G | RW1 manufactured by Qiagen Inc. | Washing solution B-1 | RNase-Free water |
| H | Washing solution B-1 | Washing solution B-1 | RNase-Free water |
| I | RW1 manufactured by Qiagen Inc. | RPE manufactured by Qiagen Inc. | RNase-Free water |
| J | RPE manufactured by Qiagen Inc. | RPE manufactured by Qiagen Inc. | RNase-Free water |
| K | RW1 manufactured by Qiagen Inc. | Washing solution B-1 | RNase-Free water |
| L | Washing solution B-1 | Washing solution B-1 | RNase-Free water |
| M | RW1 manufactured by Qiagen Inc. | RPE manufactured by Qiagen Inc. | RNase-Free water |
| N | RPE manufactured by Qiagen Inc. | RPE manufactured by Qiagen Inc. | RNase-Free water |
| O | RW1 manufactured by Qiagen Inc. | Washing solution B-1 | RNase-Free water |
| P | Washing solution B-1 | Washing solution B-1 | RNase-Free water |

RW1 manufactured by Qiagen Inc. represents the use of RNeasy Mini Kit RW1 solution manufactured by Qiagen Inc..
RPE manufactured by Qiagen Inc. represents the use of RNeasy Mini Kit RPE solution manufactured by Qiagen Inc..
RNase-Free water represents the use of RNeasy Mini Kit RW1 RNase-Free water manufactured by Qiagen Inc..

The recovered amount of the recovered RNA in Example 1-7 are shown in Table 1-5

TABLE 1-5

| Sample | Amount of Recovered RNA (μg) |
|--------|------------------------------|
| A | 12.3 |
| B | 13.0 |
| C | 15.5 |
| D | 17.1 |
| E | 20.2 |
| F | 21.3 |
| G | 20.8 |
| H | 23.5 |
| I | 12.2 |
| J | 11.3 |
| K | 13.6 |
| L | 13.1 |
| M | 22.0 |
| N | 23.3 |
| O | 21.5 |
| P | 24.3 |

From the results of Example 1-7, it is proved that the total RNA can be effectively recovered even in above described any combinations of nucleic acid-solubilizing reagent, washing solution and recovering solution using 40 μl (104 μl/cm$^2$) of DNase solution.

Example 2

(2-1) Preparation of Cartridge for Separation and Purification of Nucleic Acid

The cartridge for separation and purification of nucleic acid, which has a portion for receiving the nucleic acid-adsorbing porous membrane having an inner diameter of 7 mm was made.

(2-2) For the nucleic acid-adsorbing porous membrane, a porous membrane which is the saponified porous membrane of triacetyl cellulose was used, and the nucleic acid-adsorbing porous membrane was received in the nucleic acid-adsorbing porous membrane accommodation portion of the cartridge for separation and purification of nucleic acid prepared in the above (2-1).

Example 2-1

(2-3) Preparation of Nucleic Acid-Solubilizing Reagent and Washing Solution

The nucleic acid-solubilizing reagent and the washing solution were prepared according to the formulation indicated below.

| (Nucleic acid-solubilizing reagent A-2) | |
|---|---|
| Guanidine hydrochloride (manufactured by Life Technology Inc.) | 382 g |
| Tris (manufactured by Life Technology Inc.) | 12.1 g |
| TritonX-100 (manufactured by ICN Biochemicals Inc.) | 10 g |
| Distilled water | Add up to 1000 mL |
| 1.0 vol % of 2-mercaptoethanol is added right before the use of nucleic acid-solubilizing reagent A-2. | |
| (Washing solution A-2) | |
| 10 mM Tris-HCL | 20 to 50% ethanol |

(2-4) Procedures for Purifying Nucleic Acid

A culture solution of human myelogenous leukemia cell (HL60) was prepared. The cells were prepared to contain $1 \times 10^6$, and were washed in the $Ca^{2+}$, $Mg^{2+}$ free-PBS. 300 g of prepared cells were centrifuged with a swing rotor at 4° C. for 5 minutes, and the floating cells were pelletized, and the supernatant was removed, and the cells were resuspended by tapping. 350 µl of a nucleic acid-solubilizing reagent solution was added thereto, and was stirred using a Voretex mixer for 1 minute. Next, 350 µl of 70% ethanol was added thereto, and was stirred using the Voretex mixer for 5 seconds. After stirring, the solution was injected into one opening of the cartridge for separation and purification of nucleic acid receiving the nucleic acid-adsorbing porous membrane, which was prepared in (2-1) and (2-2) above, afterwards a pressure difference-generating apparatus (syringe pump) was connected to the one opening to make an inside of the cartridge for separation and purification of nucleic acid into a pressurized state, so as to contact the injected sample solution containing nucleic acid with the nucleic acid-adsorbing porous membrane by passing the injected sample solution containing nucleic acid through the nucleic acid-adsorbing porous membrane and discharge them from another opening of the cartridge for separation and purification of nucleic acid. Then, 500 µl of a washing solution A-2 containing 20 to 50% ethanol was injected into the one opening of the cartridge for separation and purification of nucleic acid, afterwards a pressure difference-generating apparatus was connected to the one opening to make the inside of the cartridge for separation and purification of nucleic acid into a pressurized state, so as to pass the injected washing solution A-2 through the nucleic acid-adsorbing porous membrane and discharge them from another opening. The same procedure was repeated 3 times. Further, 100 µl of the recovering solution A-2 was injected into the one opening of the cartridge for separation and purification of nucleic acid, afterwards a pressure difference-generating apparatus was connected to the one opening to make the inside of the cartridge for separation and purification of nucleic acid into a pressurized state, so as to pass the injected recovering solution A-2 through the nucleic acid-adsorbing porous membrane and discharge them from another opening, thereby the eluted solution was recovered.

Example and Comparative Example

Each procedure was conducted under the same conditions as in the above, except that the ethanol concentration in the washing solution shown in Tables 2-1 and 2-2 (the concentration of Trix-HCl is fixed) is used.

(2-5) Agarose Gel Electrophoresis of Recovered Nucleic Acid

The amount of nucleic acid in the recovered washing solution and the recovering solution from each reagent above was obtained by calculating their fluorescent strengths from the 1% agarose gel electrophoresis so that a calibration curve of DNA and RNA was formed, where the concentration was calculated. Table 2-1 shows the concentration of DNA and RNA contained in the recovering solution, and Table 2-2 shows the concentration of DNA and RNA contained in the washing solution.

TABLE 2-1

| Ethanol Concentration in Washing Step | Amount of DNA Recovered from the Recovering solution | Amount of RNA Recovered from the Recovering solution (µg) |
|---|---|---|
| Ethanol 20% | 0.0 | 3.2 |
| Ethanol 30% | 0.2 | 9.1 |
| Ethanol 40% | 1.1 | 8.4 |
| Ethanol 50% | 2.0 | 9.2 |
| Ethanol 70% | 5.2 | 10.5 |

TABLE 2-2

| Ethanol Concentration in Washing Step | Amount of DNA Recovered from the Washing solution | Amount of RNA Recovered from the Washing solution (µg) |
|---|---|---|
| Ethanol 20% | 5.1 | 9.8 |
| Ethanol 30% | 5.0 | 0.1 |
| Ethanol 40% | 2.1 | 0.5 |
| Ethanol 50% | 2.0 | 0.4 |
| Ethanol 70% | 1.8 | 0.6 |

As clearly shown from the results of Tables 2-1 and 2-2, when the ethanol concentration in the washing step was 50% by weight or less, the amount of DNA incorporated was low. From this result, according to the method of the invention, it was found that RNA can be selectively recovered by reducing the DNA incorporated in the recovering solution containing nucleic acid.

Meanwhile, it was recognized that when the ethanol concentration in the washing solution is higher than 50% by weight, DNA contamination was increased.

Example 2-2-1

(2-6) Preparation of Nucleic Acid-Solubilizing Reagent Solution and Washing Solution The nucleic acid-solubilizing reagent solution and the washing solution were prepared according to the formulation indicated below.

| (Nucleic Acid-Solubilizing Reagent Solution B-2-1) | |
|---|---|
| Guanidine thiocyanate (manufactured by Wako Pure Chemical Industries, Ltd.) | 3.5 M |
| BisTris (manufactured by Dojindo Laboratories) | 0.25 M |
| Hydrochloric acid is used to prepare the solution in pH 6.5 | |
| 1.0 vol % of 2-mercaptoethanol is added right before the use of nucleic acid-solubilizing reagent B-2-1. | |
| (Nucleic Acid Solubilizing Sample Solution B-2-2) | |
| Tween20 (manufactured by Wako Pure Chemical Industries, Ltd.) | 15% |
| BisTris (manufactured by Dojindo Laboratories) | 0.1 M |
| Hydrochloric acid is used to prepare the solution in pH 6.0 | |
| (Washing solution B-2) | |
| Tris-HCl (pH 7.5) | 10 mM |
| Sodium chloride | 0.5 M |
| Ethanol | 5 to 12.5% |
| (Recovering solution B-2) | |
| Tris-HCl (pH 6.5) | 1 mM |

(2-7) Preparation of Animal Tissue Nucleic Acid Mixture Solution

A mouse liver quickly frozen under liquid nitrogen was cut into small pieces, and 5 mg thereof was incubated in a 1.5 ml tube. 350 µl of a nucleic acid-solubilizing reagent-B-2-1 was added thereto, and was put into a Rotor-Stator Homogenizer (Polytron, manufactured by KINEMATICA, Inc.) until the mixture became homogeneous. The solution was then centrifuged at 8000×g for 3 minutes at room temperature, and the supernatant was transferred to a new 1.5 ml tube not so as to take the tissue fragments. 175 µl of a nucleic acid-solubilizing reagent B-2-2 was added thereto, and was stirred using a Voretex mixer for 15 seconds. Further, 175 µl of 99.5% or more superhigh grade ethanol was added thereto, and was stirred using the Voretex mixer for 1 minute.

(2-8) Procedures for Separating and Purifying RNA

The solution was injected into one opening of the cartridge for separation and purification of nucleic acid comprising the nucleic acid-adsorbing porous membrane as prepared in the above (2-1) and (2-2), afterwards a pressure difference-generating apparatus (syringe pump) was connected to the one opening to make an inside of the cartridge for separation and purification of nucleic acid into a pressurized state, so as to contact the injected sample solution containing nucleic acid with the nucleic acid-adsorbing porous membrane by passing the injected sample solution containing nucleic acid through the nucleic acid-adsorbing porous membrane and discharge them from another opening of the cartridge for separation and purification of nucleic acid. Then, 750 µl of a washing solution B-2 containing 5 to 12.5% ethanol was injected into the one opening of the cartridge for separation and purification of nucleic acid, afterwards a pressure difference-generating apparatus was connected to the one opening to make the inside of the cartridge for separation and purification of nucleic acid into a pressurized state, so as to pass the injected washing solution B-2 through the nucleic acid-adsorbing porous membrane and discharge them from another opening. The same procedure was repeated 3 times. Further, 100 µl of the recovering solution B-2 was injected into the one opening of the cartridge for separation and purification of nucleic acid, afterwards a pressure difference-generating apparatus was connected to the one opening to make the inside of the cartridge for separation and purification of nucleic acid into a pressurized state, so as to pass the injected recovering solution B-2 through the nucleic acid-adsorbing porous membrane and discharge them from another opening, thereby the eluted solution was recovered.

Example 2-2-2

Each procedure was conducted in the same manner as in the above (2-8), except that 30, 20, and 0% of ethanol concentration was used in the washing solution B-2.

(2-9) Agarose Gel Electrophoresis of Recovered Nucleic Acid

Figure 7:
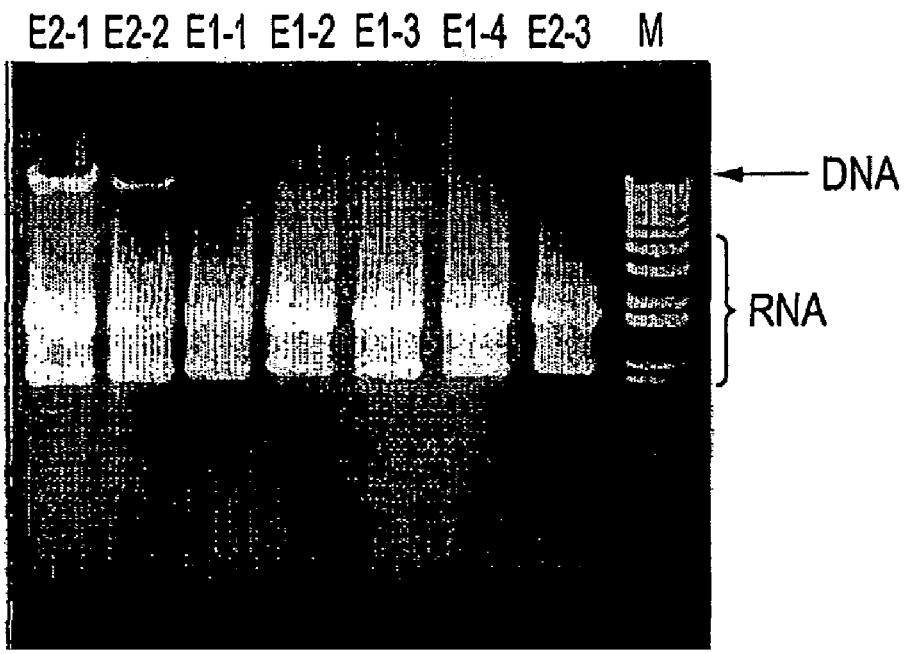
FIG. 7 is a view of the results of 1% agarose gel electrophoresis of nucleic acid purified in Example 2-2-1 and Example 2-2-2.

Nucleic acid purified in Example 2-2-1 and Example 2-2-2 was subjected to 1% agarose gel electrophoresis. The results are shown in FIG. 7.

(2-10) Amount of Recovered Nucleic Acid

The concentration of the recovering solution containing nucleic acid recovered in Example 2-2-1 and Example 2-2-2 was measured. The measurement was conducted by using absorbance at the wavelength of 260 nm. The results are shown in Table 2-3.

TABLE 2-3

| | Ethanol concentration | Amount of Recovered RNA |
|---|---|---|
| E2-1 | 30.0% | 23.1 µg |
| E2-2 | 20.0% | 21.7 µg |
| E1-1 | 12.5% | 23.9 µg |
| E1-2 | 10.0% | 24.9 µg |
| E1-3 | 7.5% | 23.2 µg |
| E1-4 | 5.0% | 20.7 µg |
| E2-3 | 0% | 19.0 µg |

As shown from FIG. 7, it is found that in the washing step of Example 2-2-1, wherein the concentration of ethanol is 5 to 12.5%, the incorporation of DNA is hardly recognized. Meanwhile, in the washing step of Example 2-2-2, wherein the concentration of ethanol is 20 to 30%, the incorporation of DNA is recognized. Further, in the case of having 0% concentration of ethanol in Example 2-2-2, although the incorporation of DNA is not recognized, the amount of nucleic acid discharged is being lowered.

According to the present invention, the amount of DNA incorporated in the recovering solution is reasonably decreased, and RNA can be selectively recovered with high yield.

INDUSTRIAL APPLICABILITY

According to the present invention, RNA can be selectively purified more inexpensively and with excellent purity from a mixture sample of DNA and RNA by using a porous membrane having an excellent separating capability, a good washing efficiency, a simple and rapid workability and a good suitability for automation and miniaturization, and capable of being mass produced with a substantially identical separating capability.

Further, RNA or DNA can be selectively recovered from a mixture sample of DNA and RNA more inexpensively and easily, by using a method for separating and purifying nucleic acid wherein the method employs the nucleic acid-adsorbing porous membrane.

The entire disclosure of each and every foreign patent application from which the benefit of foreign priority has been claimed in the present application is incorporated herein by reference, as if fully set forth.

The invention claimed is:

1. A method for selectively separating and purifying RNA from a mixture solution of nucleic acid containing DNA and RNA,
   the method using a cartridge for separation and purification of nucleic acid comprising a container having at least two openings, and the container receives a nucleic acid-adsorbing porous membrane which a solution can pass through,
   wherein the method comprising the steps of:
   (1-a) adsorbing nucleic acid to the nucleic acid-adsorbing porous membrane;
   (1-b) washing the nucleic acid-adsorbing porous membrane by a washing solution, while the nucleic acid is adsorbed to the nucleic acid-adsorbing porous membrane;
   (1-c) subjecting the nucleic acid-adsorbing porous membrane to a DNase treatment;
   (1-d) washing the nucleic acid-adsorbing porous membrane with the washing solution; and
   (1-e) desorbing the RNA from the nucleic acid-adsorbing porous membrane by a recovering solution, so as to discharge the recovering solution out of the cartridge, resulting in separated and purified RNA,
   wherein in the step (1-c), a total amount of a DNase solution is 130 µl or less per 1 cm2 of the nucleic acid-adsorbing porous membrane, and
   wherein the nucleic acid adsorbing porous membrane has (a) a front area and a back area asymmetrical with each other and (b) comprises an organic material obtained by saponification of a mixture of acetyl celluloses different from each other in acetyl value.

2. The method for selectively separating and purifying RNA according to claim 1, wherein the DNase solution has a DNase concentration of 10 to 10000 Kunitz U/mL.

3. The method for selectively separating and purifying RNA according to claim 1, wherein the mixture solution of nucleic acid is a solution where a water-soluble organic solvent is further added to a mixed solution obtained by mixing a nucleic acid solubilizing reagent added to a test sample with the test sample.

4. The method for selectively separating and purifying RNA according to claim 3, wherein the test sample is a cultured cell.

5. The method for selectively separating and purifying RNA according to claim 4, wherein the cultured cell is a cell grown in a suspension.

6. The method for selectively separating and purifying RNA according to claim 4, wherein the cultured cell is a cell grown in a monolayer.

7. The method for selectively separating and purifying RNA according to claim 3, wherein the test sample is an animal tissue.

8. The method for selectively separating and purifying RNA according to claim 3, wherein the test sample is homogenized before or after adding nucleic-acid solubilizing reagent.

9. The method for selectively separating and purifying RNA according to claim 3, wherein the nucleic acid-solubilizing reagent comprises at least one of a chaotropic salt, a nucleic acid stabilizing agent, a surfactant, a buffer and a defoaming agent.

10. The method for selectively separating and purifying RNA according to claim 9, wherein the chaotropic salt is at least one of a guanidine hydrochloride and a guanidine thiocyanate.

11. The method for selectively separating and purifying RNA according to claim 3, wherein the water-soluble organic solvent comprises at least one of methanol, ethanol, propanol and an isomer thereof, and butanol and an isomer thereof.

12. The method for selectively separating and purifying RNA according to claim 1, wherein the washing solution is a solution containing at least one alcohol selected from methanol, ethanol, propanol and an isomer thereof, and butanol and an isomer thereof, and wherein the washing solution contains said at least one alcohol in an amount of 1 to 100% by weight.

13. The method for selectively separating and purifying RNA according to claim 1, wherein the recovering solution is a solution having a salt concentration of 0.5 mol/L or less.

14. The method for selectively separating and purifying RNA according to claim 1, wherein a pressure difference-generating apparatus is detachably connected to one opening of the cartridge for separation and purification of nucleic acid.

15. An automated apparatus for selective separation and purification of RNA from a mixture solution of nucleic acids containing DNA and RNA comprising:
    a cartridge comprising a container having at least two openings and a nucleic acid-adsorbing porous membrane comprised of an organic polymer inside said container, wherein said organic polymer has hydroxyl groups which adsorbs a nucleic acid, and wherein the nucleic acid adsorbing porous membrane has a front area and a back area asymmetrical with each other and comprises an organic material obtained by saponification of a mixture of acetyl celluloses different from each other in acetyl value, and
    a pressure difference-generating device connected to one of said openings.

16. A method for selectively separating and purifying RNA or DNA, which comprises the steps of:
    (2-a) adsorbing nucleic acid to a nucleic acid-adsorbing porous membrane by passing a mixture solution of nucleic acid containing RNA and DNA through the nucleic acid-adsorbing porous membrane;
    (2-b) washing the nucleic acid-adsorbing porous membrane by passing a washing solution through the nucleic acid-adsorbing porous membrane, while the nucleic acid is adsorbed to the nucleic acid-adsorbing porous membrane; and
    (2-c) desorbing the nucleic acid from the nucleic acid-adsorbing porous membrane by passing a recovering solution through the nucleic acid-adsorbing porous membrane, resulting in the separated and purified RNA or DNA,
    wherein the washing solution contains a water-soluble organic solvent having a concentration of 50% by weight or less, and the washing solution does not contain a chaotropic salt and
    wherein the nucleic acid-adsorbing porous membrane has (a) a front area and a back area asymmetrical with each other and (b) comprises an organic material obtained by saponification of a mixture of acetyl celluloses different from each other in acetyl value.

17. The method for selectively separating and purifying RNA or DNA according to claim 16, wherein the washing solution contains a water-soluble organic solvent having a concentration of 5 to 40% by weight.

18. The method for selectively separating and purifying RNA or DNA according to claim 16, wherein the mixture of nucleic acid containing RNA and DNA is a solution where a water-soluble organic solvent is added to a solution obtained by treating a cell or virus-containing test sample with a nucleic acid-solubilizing reagent.

19. The method for selectively separating and purifying RNA or DNA according to claim 18, wherein the test sample is a cultured cell.

20. The method for selectively separating and purifying RNA or DNA according to claim 18, wherein the test sample is an animal tissue.

21. The method for selectively separating and purifying RNA or DNA according to claim 18, wherein the test sample is homogenized before or after adding nucleic-acid solubilizing reagent.

22. The method for selectively separating and purifying RNA or DNA according to claim 18, wherein the nucleic acid-solubilizing reagent comprises at least one of a chaotropic salt, a nucleic acid stabilizing agent, a surfactant, a buffer and a defoaming agent.

23. The method for selectively separating and purifying RNA or DNA according to claim 22, wherein the chaotropic salt is at least one of a guanidine hydrochloride and a guanidine thiocyanate.

24. The method for selectively separating and purifying RNA or DNA according to claim 16, wherein the water-soluble organic solvent is at least one alcohol selected from methanol, ethanol, propanol and an isomer thereof, and butanol and an isomer thereof.

25. The method for selectively separating and purifying RNA or DNA according to claim 16, wherein the washing solution is a solution containing at least one alcohol selected from methanol, ethanol, propanol and an isomer thereof, and butanol and an isomer thereof in an amount of 5 to 50% by weight.

26. The method for selectively separating and purifying RNA according to claim 16, wherein the washing solution contains water-soluble salt.

27. The method for selectively separating and purifying RNA according to claim 26, wherein the concentration of water-soluble salt is 10 mmol/L or more.

28. The method for selectively separating and purifying RNA according to claim 26, wherein the concentration of water-soluble salt is in a range of 10 mmol/L to 1 mol/L.

29. The method for selectively separating and purifying RNA or DNA according to claim 16, wherein the washing solution is a solution containing a chloride in an amount of 10 mmol/L to 1 mol/L.

30. The method for selectively separating and purifying RNA or DNA according to claim 16, wherein the recovering solution is a solution capable of desorbing an adsorbed RNA from the nucleic acid-adsorbing porous membrane having a salt concentration of 0.5 mol/L or less.

31. The method for selectively separating and purifying RNA or DNA according to claim 16, wherein in each of the steps of (2-a), (2-b) and (2-c), the sample solution containing the nucleic acid, the washing solution and the eluting solution are passed through the nucleic acid-adsorbing porous membrane by using (i) a cartridge for separation and purification of nucleic acid comprising a container having at least two openings, and the cartridge for separation and purification of nucleic acid receives the nucleic acid-adsorbing porous membrane which a solution can pass through in the container and (ii) a pressure difference-generating apparatus, and wherein the pressure difference-generating apparatus is a pump detachably connected to one opening of the cartridge for separation and purification of nucleic acid.

32. A kit comprising:
- a cartridge for selective separation and purification of nucleic acid wherein the cartridge comprises a container having at least two openings and a nucleic acid-adsorbing porous membrane comprising an organic polymer inside said container, wherein said organic polymer has hydroxyl groups which adsorbs a nucleic acid, and wherein the nucleic acid-adsorbing porous membrane has a front area and a back area asymmetrical with each other and comprises an organic material obtained by saponification of a mixture of acetyl celluloses different from each other in acetyl value,
- a nucleic acid-solubilizing reagent comprising at least one of a chaotropic salt, a nucleic acid stabilizing agent, a surfactant, a buffer, and a defoaming agent, and
- a pressure difference-generating apparatus.

* * * * *